(12) United States Patent
Cuppoletti et al.

(10) Patent No.: US 11,833,503 B2
(45) Date of Patent: Dec. 5, 2023

(54) METHODS AND COMPOSITIONS FOR SURFACE FUNCTIONALIZATION OF OPTICAL SEMICONDUCTOR-INTEGRATED BIOCHIPS

(71) Applicant: InSilixa, Inc., Sunnyvale, CA (US)

(72) Inventors: Andrea Cuppoletti, Livermore, CA (US); Arjang Hassibi, Santa Clara, CA (US); Lei Pei, San Jose, CA (US); Yang Liu, San Jose, CA (US); Kshama Jirage, Palo Alto, CA (US); Arun Manickam, San Jose, CA (US)

(73) Assignee: InSilixa, Inc., Sunnyvale, CA (US)

( * ) Notice: Subject to any disclaimer, the term of this patent is extended or adjusted under 35 U.S.C. 154(b) by 0 days.

(21) Appl. No.: 17/544,776

(22) Filed: Dec. 7, 2021

(65) Prior Publication Data

US 2023/0173483 A1    Jun. 8, 2023

(51) Int. Cl.
| | | |
|---|---|---|
| *B01L 3/00* | (2006.01) | |
| *H01L 27/146* | (2006.01) | |
| *C23C 16/02* | (2006.01) | |
| *C07F 7/08* | (2006.01) | |
| *B01L 7/00* | (2006.01) | |

(52) U.S. Cl.
CPC ... *B01L 3/502715* (2013.01); *B01L 3/502707* (2013.01); *B01L 3/502738* (2013.01); *B01L 7/52* (2013.01); *C07F 7/089* (2013.01); *C23C 16/0272* (2013.01); *H01L 27/14645* (2013.01); *B01L 2200/0689* (2013.01);
(Continued)

(58) Field of Classification Search
CPC ......... B01L 3/502715; B01L 3/502707; B01L 3/502738; B01L 7/52; B01L 2200/0689; B01L 2300/0663; B01L 2300/0819; B01L 2300/0883; B01L 2400/06; C07F 7/089; C23C 16/0272; H01L 27/14645
See application file for complete search history.

(56) References Cited

U.S. PATENT DOCUMENTS

| | | | | |
|---|---|---|---|---|
| 5,002,622 A | * | 3/1991 | Gregg | G11B 7/26 |
| | | | | 156/243 |
| 6,074,962 A | * | 6/2000 | Sakamoto | H01L 21/316 |
| | | | | 438/782 |

(Continued)

FOREIGN PATENT DOCUMENTS

| | | |
|---|---|---|
| WO | WO-2017004463 A1 | 1/2017 |
| WO | WO-2023107963 A1 | 6/2023 |

OTHER PUBLICATIONS

Brittain, W. J. et al., The Surface Science of Microarray Generation—A Critical Inventory, ACS Appl Mater Interfaces. Oct. 30, 2019;11(43):39397-39409.

(Continued)

*Primary Examiner* — Dale E Page
*Assistant Examiner* — Quovaunda Jefferson
(74) *Attorney, Agent, or Firm* — WILSON SONSINI GOODRICH & ROSATI

(57) ABSTRACT

The present disclosure provides methods and compositions for surface functionalization of solid substrates. The compositions include functionalized silanes and nucleic acid constructs which may react to immobilize the nucleic acid constructs on the surface on the solid substrate. The disclosure also provides methods for immobilization of silanes and nucleic acid constructs on the surface of the substrate.

14 Claims, 11 Drawing Sheets

(52) U.S. Cl.
CPC .............. *B01L 2300/0663* (2013.01); *B01L 2300/0819* (2013.01); *B01L 2300/0883* (2013.01); *B01L 2400/06* (2013.01)

(56) References Cited

U.S. PATENT DOCUMENTS

| | | | | |
|---|---|---|---|---|
| 6,407,006 | B1* | 6/2002 | Levert | B82Y 10/00 |
| | | | | 257/E21.243 |
| 7,541,176 | B2* | 6/2009 | Raynor | G01J 3/02 |
| | | | | 435/287.2 |
| 9,447,455 | B2* | 9/2016 | Hu | C07D 207/408 |
| 2005/0233473 | A1 | 10/2005 | Cicero et al. | |
| 2013/0338044 | A1* | 12/2013 | Liao | G01N 33/54353 |
| | | | | 534/550 |
| 2016/0200847 | A1* | 7/2016 | Chiari | C09D 133/26 |
| | | | | 506/9 |
| 2018/0327832 | A1* | 11/2018 | Ramirez | C12Q 1/6806 |

OTHER PUBLICATIONS

Davydova, M. et al., Catalyst-free site-specific surface modifications of nanocrystalline diamond films via microchannel cantilever spotting. RSC Adv., 2016,6, 57820-57827.

Frydrych-Tomczak, E. et al., "Structure and oligonucleotide binding efficiency of differently prepared click chemistry-type DNA microarray slides based on 3-azidopropyltrimethoxysilane", Materials, May 26, 2021, vol. 14, 2855, pp. 1-14.

PCT/US2022/081038 International Search Report and Written Opinion dated Apr. 17, 2023.

* cited by examiner

HybC1

HybC1-TEG

HybC2

NP

METHODS AND COMPOSITIONS FOR SURFACE FUNCTIONALIZATION OF OPTICAL SEMICONDUCTOR-INTEGRATED BIOCHIPS

BACKGROUND

The surfaces of optical complementary metal-oxide-semiconductor (CMOS) biochips can be biofunctionalized with modified silanes to covalently react with complementary chemically modified nucleic acid constructs. However, known methods for surface functionalization of CMOS substrates suffer from several deficiencies such as requiring the use of highly reactive chemical species, requiring unfavorable reactions conditions such as high temperature or pH, and being difficult to control spatially.

SUMMARY

The present disclosure provides chemical compounds and methods for the surface functionalization of CMOS biosensor arrays and related substrates. The compositions as disclosed herein comprise functionalized silanes and functionalized nucleic acid constructs. Functionalized silanes and nucleic acid constructs may be designed with complementary chemical groups which react to form a covalent bond when contacted. The present disclosure further provides methods for the preparation of such modified silanes and nucleic acids constructs as well as methods for their surface immobilization.

In an aspect, the present disclosure provides for a method for immobilizing a nucleic acid construct to a surface of a substrate, the method comprising: (a) immobilizing a silane to the surface of the substrate, wherein the silane comprises a first chemical group; and (b) contacting the silane with the nucleic acid construct comprising a second chemical group; wherein the substrate comprises an integrated optical sensor circuit wherein the first chemical group reacts with the second chemical group via an azide-alkyne cycloaddition, thereby immobilizing the nucleic acid construct on the substrate.

In some embodiments, the integrated optical sensor circuit comprises a complementary metal-oxide-semiconductor (CMOS) integrated circuit (IC). In some embodiments, the integrated optical sensor circuit is configured for optical transduction of a fluorescent signal. In some embodiments, the azide-alkyne cycloaddition is a strain-promoted alkyne-azide cycloaddition (SPAAC). In some embodiments, the first chemical group comprises a first alkyne and the second chemical group comprise a first azide; or (2) the first chemical group comprises a second azide and the second chemical group comprises a second alkyne. In some embodiments, the first and second alkyne is a cyclic alkyne. In some embodiments, the cyclic alkyne is a dibenzocyclooctyne (DBCO), or a derivative thereof. In some embodiments, the immobilizing in (a) comprises depositing the silane onto the surface of the substrate. In some embodiments, the depositing comprises a vapor deposition. In some embodiments, the depositing comprises a liquid deposition. In some embodiments, the silane further comprises an alkoxy moiety. In some embodiments, (1) the first chemical group further comprises a first linker, or (2) the second chemical group further comprises a second linker. In some embodiments, the first linker and the second linker comprises a polyethylene glycol (PEG) moiety. In some embodiments, the contacting in (b) is carried out at neutral pH. In some embodiments, the contacting in (b) is carried out at room temperature. In some embodiments, the contacting in (b) is carried out for less than about 10 minutes. In some embodiments, the contacting in (b) is carried out for less than about 30 minutes. In some embodiments, the contacting in (b) is carried out for less than about 60 minutes. In some embodiments, the contacting in (b) is carried out for less than about 2 hours. In some embodiments, the contacting in (b) is carried out for less than about 4 hours. In some embodiments, the contacting in (b) is carried out for less than about 8 hours. In some embodiments, the method further comprises: (c) washing the surface of the substrate. In some embodiments, the method further comprises prior to (b) repeating (a) with the silane or a different silane. In some embodiments, the contacting in (b) further comprises contacting the silane with at least one additional nucleic acid construct.

In another aspect, the present disclosure provides for a method for immobilizing a nucleic acid construct to a surface of a substrate at a surface density, the method comprising: (a) immobilizing a coating to the surface of the substrate, wherein the coating comprises a first chemical group; (b) repeating (a), thereby achieving a target density of the coating on the surface of the substrate; and (c) contacting the coating with a mixture comprising the nucleic acid construct at a concentration, wherein the nucleic acid construct comprises a second chemical group, thereby achieving the surface density of the nucleic acid construct on the surface of the substrate; wherein the first chemical group and the second chemical group react via a chemical reaction, and wherein the substrate comprises an integrated optical sensor circuit.

In some embodiments, the surface density of the nucleic acid construct is determined by a time of hybridization of a complementary nucleic acid construct, a fluorescence amplitude as a function of PCR heating cycle, a percent quenching, or an area of quenching. In some embodiments, the integrated optical sensor circuit comprises a complementary metal-oxide-semiconductor (CMOS) integrated circuit (IC). In some embodiments, the integrated optical sensor circuit is configured for optical transduction of a fluorescent signal. In some embodiments, the mixture further comprises another nucleic acid construct. In some embodiments, the chemical reaction comprises an azide-alkyne cycloaddition. In some embodiments, the chemical reaction comprises a nucleophilic attack of an epoxide.

In another aspect, the present disclosure provides for a composition comprising: an integrated optical biochip comprising a surface; and a coating deposited on the surface; wherein the coating comprises a silane comprising an azide. In some embodiments, the coating comprises a molecule of the formula:

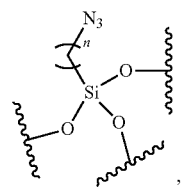

wherein n is an integer from 1-20.

In another aspect, the present disclosure provides for a composition comprising: an integrated optical biochip comprising a surface; and a coating deposited on the surface; wherein the coating comprises a strained alkyne.

In some embodiments, the coating further comprises a modified silane. In some embodiments, the strained alkyne is a strained cycloalkyne. In some embodiments, strained cycloalkyne is a derivative of dibenzocyclooctyne (DBCO). In some embodiments, the coating further comprises a linker. In some embodiments, the coating comprises a molecule of the formula

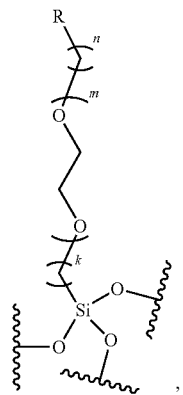

wherein k and n are integers independently selected from 1-20, m is an integer selected from 2-5, and R is a derivative of DBCO.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
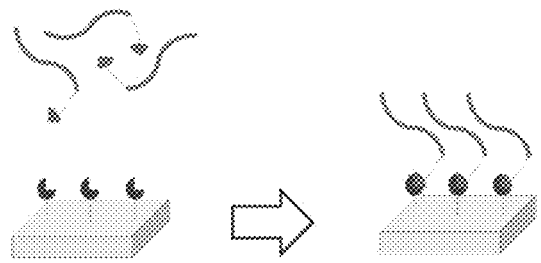
FIG. 1 shows a schematic representation of covalent probe immobilization on a surface.

Aspects of the present disclosure provide for the specific covalent immobilization of molecular probes onto the planar surface of a complementary metal-oxide-semiconductor (CMOS) device, herein referred to as a CMOS substrate. The surface of CMOS substrates is typically made of electrically non-conductive materials, generally referred to as the passivation layer, which can include very large-scale integration (VLSI) compatible dielectric oxides such as $SiO_2$ and $Si_3N_4$.

There is a need for alternative method for the immobilization of molecular probes onto CMOS substrates. Such a method ideally should have the following characteristics: First, the coupling chemistry should be orthogonal to nucleophiles present on oligonucleotides (amine groups, hydroxy groups, etc.), removing the need to block unreacted groups on the surface. Second, the coupling reaction should not be activated by or require an extreme pH. Finally, the coupling reaction should be quantitative and extremely rapid, with no need to incubate for a long time (e.g., overnight).

Azide groups react rapidly and quantitatively with strained cyclic alkynes, generating a stable cycloadduct. Moreover, such chemical groups have minimal reactivity towards oligonucleotide functional groups (primary amines, secondary amines, primary alcohols, secondary alcohols, phosphates, ketones, aldehydes, etc.). A strained cyclicalkyne and an azide can be used to create bio-orthogonal reactions for the functionalization of biomolecules. Accordingly, the use of azide and/or strained cyclic alkynyl modifications on molecular probes or CMOs substrates can serve as an appropriate way of functionalizing the surface of substrates.

Substrates

The present disclosure provides methods and compositions for coating the surface of solid substrates, such as integrated optical sensor circuits. The integrated optical sensor circuit may comprise a CMOS substrate. A CMOS substrate may be the solid and planar surface of a semiconductor device that is fabricated using complementary metal-oxide-semiconductor microfabrication processes. Such a device may have dimensions (width and length) between 0.5 mm to 25 mm and a thickness of between 0.05 mm to 1.5 mm. The surface of CMOS substrates may be microfabricated using planar very large-scale integration (VLSI) processes to have electrically non-conductive materials, generally referred to as the passivation layer. In some cases, the passivation layer on the CMOS substrate is optically transparent to allow the CMOS device to perform optical detection (e.g., of a fluorescent signal). Example materials for the passivation layer are thin oxides such as $SiO_2$ and $Si_3N_4$.

Substrates as described herein may be part of an optical biochip system. An optical biochip system may comprise a CMOS biosensor array that uses optical detection methods, such as inverse fluorescence transduction (IFT) (see, e.g., U.S. Pat. No. 9,133,504 and Hassibi, A et al. *Nat. Biotechnol.* 2018, 36(8), 738-745). Such optical biochip systems may be part of systems or used in methods for molecular detection assays in life-science research and diagnostics, such as applications using nucleic acid molecules s their detection targets or molecular recognition elements (e.g., probe). Some examples of such applications are nucleic acid amplification tests that use polymerase chain reaction processes, affinity-based detection systems that take advantage of 2-dimensional and addressable DNA microarrays, and DNA sequencing arrays that incorporate solid-phase sequencing by synthesis (SBS) methods.

Silanes and Modified Silanes

Silanes as described herein may comprise molecules comprising at least one silicon atom with four bonds to other atoms such as carbon, hydrogen, and oxygen. Silanes as described herein may further comprise one or more chemical groups. Alternatively or additionally, silanes of the present disclosure may comprise one or more linkers. A silane that comprises one or more reactive chemical groups and/or linkers as described herein may be described as a "modified silane." Silanes may comprise an alkyl, alkenyl or alkynyl silane or derivatives thereof. Silanes may comprise one or more alkoxy groups. For example, silanes may comprise methoxy silanes, dimethoxy silanes, trimethoxy silanes, ethoxy silanes, diethoxy silanes, triethoxy silanes, derivatives thereof, and the like. In some cases, silanes comprising alkoxy groups as described herein may crosslink with other silanes and/or an $SiO_2$ surface.

In some cases, the silane or modified silane may comprise a molecule of Formula (I) below:

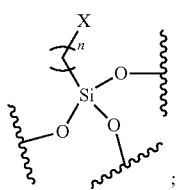

Formula (I)

wherein: n is an integer from 1-20 and X is a reactive chemical group such as azide, alkynyl, strained alkynyl, cycloalkynyl, strained cycloalkynyl (e.g., DBCO) or a derivative thereof.

In some cases, the silane or modified silane may comprise a molecule of Formula (II) below:

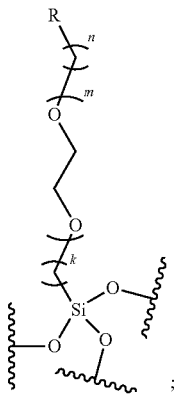

Formula (II)

wherein: k and n are integers independently selected from 1-20, m is an integer selected from 2-5, and R is a reactive chemical group such as azide, alkynyl, strained alkynyl, cycloalkynyl, strained cycloalkynyl (e.g., DBCO) or a derivative thereof.

Linkers

Molecules as described herein (e.g., modified silanes, nucleic acid constructs) may comprise one or more linkers. Linkers may, for example, increase the distance between a nucleic acid construct and the surface of a substrate. Alternatively or additionally, a linker may separate the rest of a nucleic acid construct from a label (e.g., fluorescent label).

The precise distances or separation a linker effects between one part of molecule and another may be varied for different reaction systems to obtain optimal results. In some cases, a linkage that maintains a nucleotide at some distance form a surface of a substrate may be desired. The length of a may be, for example, 1-100 atoms in length, or 1-50 atoms in length, or 1-40 atoms in length, or 2-35 atoms in length, or 3 to 30 atoms in length, or 5 to 25 atoms in length, or 10 to 20 atoms in length, etc.

Linkers may comprise any number of basic chemical starting blocks. For example, linkers may comprise linear or branched alkyl, alkenyl, or alkynyl chains, or combinations thereof. Such linkers may have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more atoms. A linker may comprise a polyoxyethylene chain (also commonly referred to as polyethyleneglycol, or PEG). A PEG linker as disclosed herein may comprise repeating units of ethylene glycol. In some cases, a PEG linker may comprise 1, 2, 3, 4, 5, 6, 7, 8, 9, 10, 11, 12, 13, 14, 15, 16, 17, 18, 19, 20, or more ethylene glycol units.

The linker may be rigid in nature or flexible. Rigid structures include laterally rigid chemical groups, e.g., ring structures such as aromatic compounds, multiple chemical bonds between adjacent groups, e.g., double or triple bonds, in order to prevent rotation of groups relative to each other, and the consequent flexibility that imparts to the overall linker. Thus, the degree of desired rigidity may be modified depending on the content of the linker, or the number of bonds between the individual atoms comprising the linker. Further, addition of ringed structures along the linker may impart rigidity. Ringed structures may include aromatic or non-aromatic rings. Rings may be anywhere from 3 carbons, to 4 carbons, to 5 carbons or even 6 carbons in size. Rings may also optionally include heteroatoms such as oxygen or nitrogen and also be aromatic or non-aromatic. Rings may additionally optionally be substituted by other alkyl groups and/or substituted alkyl groups.

Linkers that comprise ring or aromatic structures can include, for example aryl alkynes and aryl amides. Other examples of the linkers of the disclosure include oligopeptide linkers that also may optionally include ring structures within their structure.

For example, in some cases, polypeptide linkers may be employed that have helical or other rigid structures. Such polypeptides may be comprised of rigid monomers, which derive rigidity both from their primary structure, as well as from their helical secondary structures, or may be comprised of other amino acids or amino acid combinations or sequences that impart rigid secondary or tertiary structures, such as helices, fibrils, sheets, or the like. By way of example, polypeptide fragments of structured rigid proteins, such as fibrin, collagen, tubulin, and the like may be employed as rigid linker molecules.

Reactive Chemical Groups

Molecules (e.g., silanes, nucleic acid constructs) of the present disclosure may comprise one or more "chemical groups" or "reactive chemical groups". Reactive chemical groups may comprise chemical functional groups or moieties which participate in characteristic chemical reactions. In some cases, reactive functional groups may comprise well-known functional groups in chemical and biochemical arts defined in terms of particular arrangements of atoms such as alkyl, alkenyl, alkynyl, phenyl, halo, hydroxyl, aldehyde, carboxylate, carboxyl, ether, epoxide, carboxamide, amidine, amine, imine, imide, azide, azo, cyanate, isocyanate, nitrate, nitrile, isonitrile, nitroso, oxime, sulfhydryl, sulfide, disulfide, sulfinyl, sulfonyl, sulfino, sulfo, thiocyanate, isothiocyanate, phosphino, phosphono, phosphate, and the like. Alternatively or additionally, classes of reactive functional groups may be defined based on the role they play in certain chemical reactions or classes of chemical reactions. For example, reactive chemical groups may comprise nucleophiles, electrophiles, dienes, dienophiles, 1,3-dipoles, dipolarophiles or other classes of functional groups known in the art to react in certain ways. In some cases, the reactive chemical group may comprise an alkyne. In some cases, the alkyne may comprise a strained alkyne. In some cases, the reactive chemical group may comprise an azide. In some cases, the reactive functional group may comprise a 1,3-dipole. In some cases, the reactive functional group may comprise a dipolarophile.

One or more chemical groups may be present on a molecule (e.g., silane, nucleic acid construct) as described herein. A chemical group may be present as a pendant chemical moiety or group. The chemical group(s) may be selected on the basis of their complementarity or orthogonality (e.g., lack of reactivity toward) with respect to other chemical group(s).

Molecules of the present disclosure may comprise any number of chemical groups such as 1, 2, 3, 4, 5, 10, 20, 50, 100, 200, 500, 1,000, 10,000, 100,000, 1,000,000, 10,000,000 or more chemical groups. Alternatively or additionally, a molecule may comprise more than one type of chemical group. For example, a molecule may comprise 1, 2, 3, 4, 5, 6, 7, 8, 9, 10, 20, 30, 40, 50, 60, 70, 80, 90, 100, or more distinct types of chemical groups.

Complementary Chemical Groups

Two chemical groups or reactive chemical groups may be described herein as "complementary chemical groups" or "complementary" if they may react to form one or more new covalent bonds. For example, a first chemical group may comprise a nucleophile (e.g., an amine) and a second chemical group may comprise an electrophile (e.g., an epoxide). Since the amine may attack the epoxide under certain ambient conditions (e.g., temperature, pH) to create a new nitrogen-carbon bond, the two chemical groups may be described as complementary herein. In another example, a first chemical group comprises an alkyne (e.g., a strained alkyne, e.g., DBCO or a derivative thereof) and a second chemical group comprises a 1,3-dipole (e.g., an azide or a derivative thereof). Since the 1,3-dipole and the alkyne may react in a 1,3-dipolar cycloaddition to form a five-member ring, the first and second chemical groups may be described as complementary herein.

In some cases, a first chemical group may comprise an azide or a strained cyclic alkyne and a second, complementary, chemical group may comprise a strained cyclic alkyne or an azide. Azide groups react rapidly and quantitatively with strained cyclic alkynes, generating a stable cycloadduct. Moreover, such chemical groups have minimal reactivity towards (e.g., are orthogonal to) oligonucleotide functional groups (e.g., primary amines, secondary amines, primary alcohols, secondary alcohols, phosphates, ketones, aldehydes, etc.).

A strained cyclic-alkyne and an azide can be used to create bio-orthogonal reactions for the functionalization of biomolecules, for example, as described in Blomquist, A. T; Liu, L. H. *J. Am. Chem. Soc.* 1953, 75, 9, 2153-2154, the entirety of which is incorporated herein by reference. Such reactions are referred to as strain-promoted [3+2] azide-alkyne cycloaddition (SPAAC) which have been utilized extensively for in-vivo conjugation, due to (i) their orthogonality with biomolecules; (ii) their high efficiency at neutral pH; and (iii) no need for a reaction catalyst, as described in Agard, N. J; Prescher, J. A; Bertozzi, C. R. *J. Am. Chem. Soc.* 2004, 126, 15046-7 and Kim, E; Koo, H. *Chem. Sci.,* 2019, 10, 7835-785, each of which are incorporated herein by reference in their entirety.

Figure 2A:
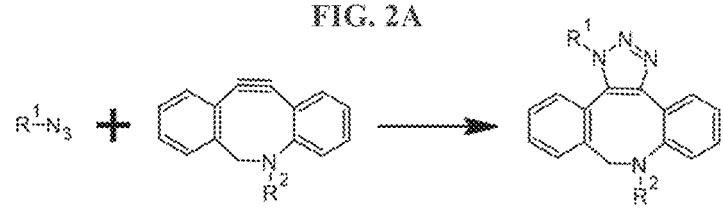
FIG. 2A shows a reaction between a substituted azide and a substituted strained alkyne.

An example of two molecules comprising complementary chemical groups is shown in FIG. 2A. One molecule comprises a first chemical group comprising a azide and a second molecule comprises a second chemical group comprising a strained cycloalkyne (DBCO). The two chemical groups react via a 1,3-dipolar cycloaddition to form a substituted 1,2,3-triazole product.

Figure 2B:
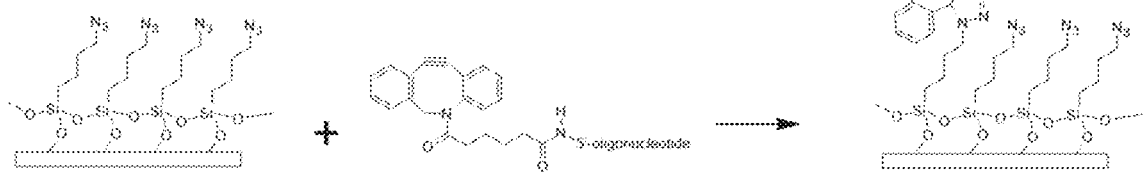
FIG. 2B shows a surface activated with silane azide reacting with oligonucleotide-5'-DBCO-functionalized.
Figure 2C:
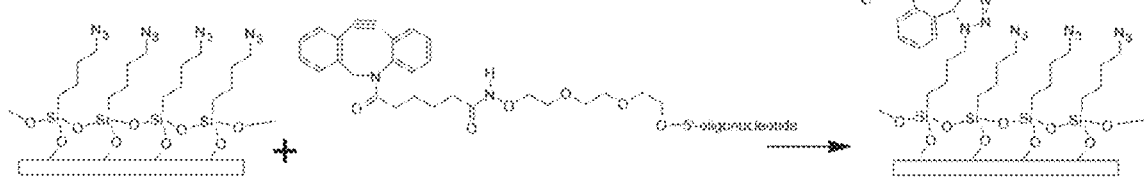
FIG. 2C shows a surface activated with silane azide reacting with oligonucleotide-5'-DBCO-TEG (10-(6-oxo-6-(dibenzo[b,f]azacyclooct-4-yn-1-yl)-capramido-N-ethyl)-O-triethyleneglycol)-functionalized.

Immobilization of Nucleic Acid Constructs by Reactions Between Complementary Chemical Groups Molecules of the present disclosure (e.g., silanes, nucleic acid constructs), may have chemical groups selected to be complementary to one another or otherwise participate in certain chemical reactions. In some cases, a reaction between two complementary chemical groups may result in the immobilization of a nucleic acid construct on the surface of a substrate. For example, FIG. 2B shows an example of a solid substrate as described herein coated with a silane comprising a first chemical group comprising an azide. Upon contact with a nucleic acid construct comprising second chemical group comprising a substituted DBCO group, the first and second chemical groups react to form a 1,2,3-triazole product, thereby immobilizing the nucleic acid to the surface of the substrate. Another example is shown in FIG. 2C in which the same solid substrate comprising a silane comprising a first chemical group comprising an azide reacts with a nucleic acid construct comprising a second chemical group comprising a substituted DBCO comprising a polyethylene glycol (PEG) linker. The two chemical groups again react to form a 1,2,3-triazole product, thereby immobilizing the nucleic acid construct on the surface of the substrate.

Figure 3:
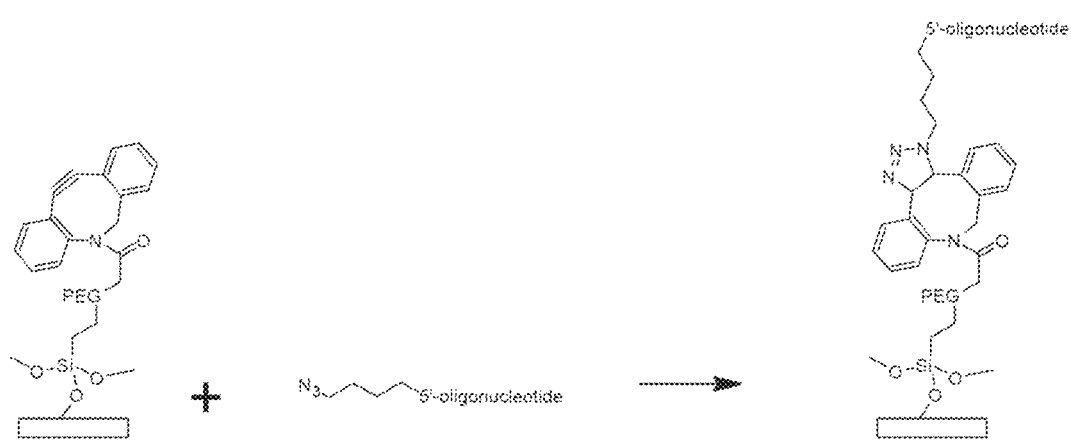
FIG. 3 shows a surface activated with silane DABCO, reacting with oligonucleotide which is functionalized in 5' with an azide moiety.

Another example is shown in FIG. 3. In this example, a substrate as described herein comprises a modified silane comprising a PEG linker and a first chemical group comprising a DBCO. A nucleic acid construct as described herein comprises a second chemical group comprising an azide. The first and the second chemical group may react as shown to form a 1,2,3-triazole product, thereby immobilizing the Methods of Immobilizing Molecules on Substrates An aspect of the present disclosure provides for methods for coating a surface of a substrate with one or more nucleic acid constructs. Example processes for coating a surface with nucleic acid constructs are illustrated in FIGS. 4A-E.

In a first step, as illustrated in each of FIGS. 4A-E, a silane is immobilized on the surface of a substrate (e.g., a CMOS substrate). In some cases, the silane is immobilized by deposition on the surface. The silane may be deposited by any suitable means such as chemical, including chemical vapor deposition (CVD), washing, plating, and other liquid depositions, or physical, such as physical vapor deposition (PVD) or sputtering. Prior to deposition of the silane, the surface of the substrate may comprise thermal grown $SiO_2$. The deposition step may be preceded by an optional oxygen plasma treatment step to generate additional silanol groups for at least about 1 minute, 2 minutes, 3 minutes, 5 minutes, 10 minutes, 15, minutes, 20 minutes, or more. A water contact angle (WCA) test can be performed to determine the hydrophobicity of the surface before and/or after the plasma treatment.

Although FIGS. 4A-E depict one silane as being immobilized, any number of silanes may be immobilized on the surface. In some cases, 1, 2, 3, 4, 5, 6, 7, 8, 9, 10, or more different silanes are immobilized on the substrate surface. One or more of the silanes may have a reactive chemical group. One or more of the silanes may lack a reactive chemical group. Different silanes may be immobilized simultaneously (e.g., in the same immobilized step) or in separate immobilization steps.

In some cases, a deposition step may comprise one or more CVD steps. CVD steps may comprise loading the substrate into a vacuum oven, loading the silane to be deposited, pumping down the vacuum of the oven, allowing the substrate to dwell, and optionally performing a WCA test to measure hydrophobicity of the surface. A deposition may be repeated more than once. For example, a deposition step may be repeated 1, 2, 3, 4, 5, 6, 7, 8, 9, 10, or more times. The substrate may be allowed to dwell in the oven for at least about 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, 120 minutes, or longer. The conditions in the oven may comprise a reduced pressure atmosphere. For example, the pressure in the over may be about 1 torr, 2 torr, 3 torr, 4 torr, 5 torr, 10 torr, 15 torr, 20 torr, 50 torr, 100 torr, 200 torr, 500 torr, or less. Alternatively or additionally, the conditions in the oven may comprise a certain temperature. The temperature in the oven may be at least about 50° C., 60° C., 70° C., 80° C., 90° C., 100° C., 110° C., 120° C., 130° C., 140° C., 150° C. or more.

Figure 4A:
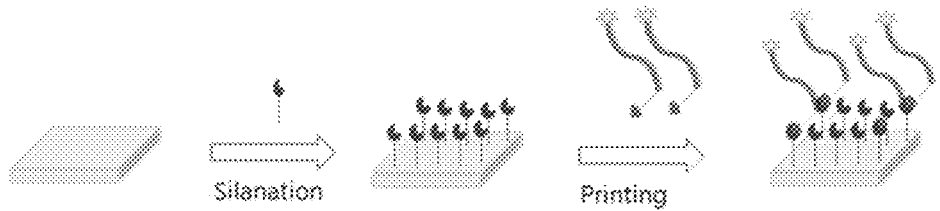
FIGS. 4A-4E shows various methods for immobilizing a nucleic acid on a substrate.
Figure 4B:
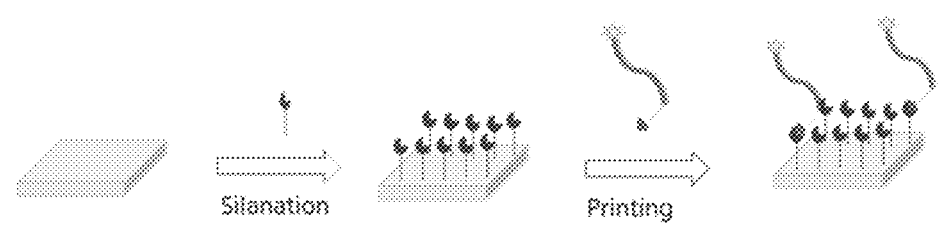
Figure 4C:
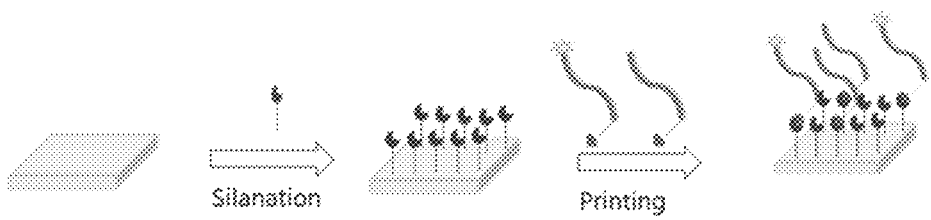
Figure 4D:
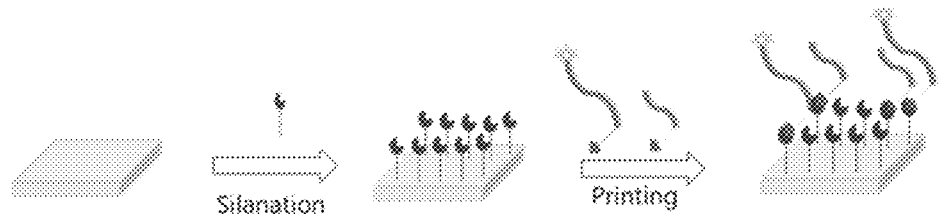
Figure 4E:
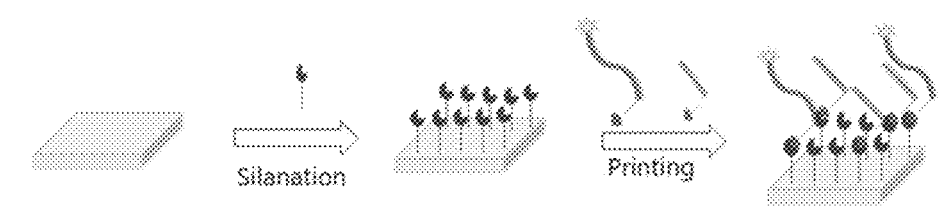

Once the silane has been immobilized on the substrate surface, the silanated surface may then be contacted with the oligonucleotide probes or other nucleic acid constructs of interest. Nucleic acid construct(s) of interest may be present in a solution (e.g., printing buffer, printing solution) in contact with the substrate. As depicted in FIGS. 4A and 4B, nucleic acid constructs may be present in the solution at various concentrations. The nucleic acid constructs may comprise a reactive functional group (depicted in FIGS. 4A-E as a wedge) that is complementary to another reactive functional group on the silanated substrate surface (depicted as a sector complementary in shape to the wedges on the nucleic acid constructs). For example, FIG. 4A depicts a case in which the printing buffer contains an oligonucleotide of interest with a fluorescent tag present in the solution at a concentration X. FIG. 4B depicts a case in which the solution contains an oligonucleotide of interest with a fluorescent tag present at a concentration X/2. Further, as illustrated in FIGS. 4C and 4D, more than one different nucleic acid construct may be present in the solution. As shown in FIG. 4C, the different nucleic acid constructs may have the same or similar sequences and/or differ by the presence or absence of a label. As shown in FIG. 4D, the different nucleic acid constructs may comprise substantially different sequences. As illustrated in FIG. 4E, the solution may comprise non-nucleic acid molecules (e.g., polyethylene glycol molecules) that have the reactive chemical group.

The concentration of target nucleic acid construct(s) in the solution may be any appropriate concentration. In some cases, the concentration of target nucleic acid construct(s) in the printing buffer ranges from about 1 µM to about 100 mM. In some cases, the concentration of target nucleic acid construct(s) in the printing buffer ranges from about 1 µM to about 25 µM. The concentration may be about 1 µM, 2 µM, 3, µM, 4, µM, 5 µM, 6 µM, 7 µM, 8 µM, 9 µM, 10 µM, 11 µM, 12 µM, 13 µM, 14 µM, 15 µM, 16 µM, 17 µM, 18 µM, 19 µM, 20 µM, 21 µM, 22 µM, 23 µM, 24 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 200 µM, 300 µM, 400 µM, 500 µM, 600 µM, 700 µM, 800 µM, 900 µM, 1 mM, 2, mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 30 mM, 35 mM, 40 mM, 45 mM, 50 mM, 60 mM, 65 mM, 70 mM, 80 mM, 85 mM, 90 mM, 95 mM, 100 mM, or more.

The solution may contain one or more distinct nucleic acid construct(s). The solution may contain 1, 2, 3, 4, 5, 6, 7, 8, 10, 20, 50, 100, 200, 500, 1,000, 10,000, or more distinct nucleic acid constructs. The nucleic acid constructs may differ in one or more of their sequences, labels, chemical modifications, reactive chemical groups, concentrations, and other properties.

In some cases, the contacting may be carried out under a certain set of conditions (e.g., temperature, pH). The conditions may correspond to ambient and/or neutral conditions. For example, the contacting may be carried out at room temperature and/or neutral pH. In some cases, the contacting may at place at about 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., or more. In some cases, the contacting may be carried out at elevated temperatures, such as about 35° C., 40° C., 45° C., 50° C., 60° C., 70° C., 80° C., 90° C., 100° C., 110° C., 120° C., 130° C., 140° C., 150° C., or more. In some cases, the contacting may be carried out at lowered temperatures such as about 10° C., 0° C., −10° C., −20° C., −30° C., −40° C., −50° C., or lower. In some cases, the contacting may take place at a pH of about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0 or more. In some cases, the contacting may take place at a pH of 6.0, 5, 5.0, 4.5, 4.0, 3.5, 3.0, 2.5, 2.0, 1.5, 1.0, 0.5, 0, or lower. In some cases, the contacting may take place at a pH of 8.0, 8.5, 9.0, 9.5, 10.0, 10.5, 11.0, 11.5, 12.0, 12.5, 13.0, 13.5, 14.0, or more.

In some cases, a contacting step may be repeated one or more times. A contacting step may be repeated 1, 2, 3, 4, 5, 6, 7, 8, 9, 10, 11, 12, 13, 14, 15, 16, 17, 18, 19, 20, or more times. In each contacting step, the solution may comprise the same nucleic acid construct(s) or it may comprise different nucleic acid construct(s).

A contacting step may further comprise an incubation period during which a chemical reaction is allowed to occur (e.g., between a first and a second chemical group). The length of an incubation period or contacting step may be determined based on the chemical reaction. In some cases, an incubation may be about 10 minutes, 20 minutes, 30 minutes, 40 minutes, 50 minutes, 60 minutes, 2 hours, 3 hours, 4, hours, 5 hours, 6 hours, 7 hours, 8 hours, 9 hours, 10 hours, 11 hours, 12 hours, 13 hours, 14 hours, 15 hours, 16 hours or more. In some cases, an incubation may be less than about 16 hours, 15 hours, 14 hours, 13 hours, 12 hours, 11 hours, 10 hours, 9 hours, 8 hours, 7 hours, 6 hours, 5 hours, 4 hours, 3 hours, 2 hours, 60 minutes, 50 minutes, 40 minutes, 30 minutes, 20 minutes, 10 minutes, or less.

In some cases, the solution comprises a printing buffer. In such cases, the contacting may comprise dispensing or printing the printing buffer containing the nucleic acid construct(s) onto the surface of a substrate by a non-contact method such as a liquid handling machine comprising piezo dispense capillaries. Such methods allow for high precision in the location at which the printing buffer is dispensed, such as on a particular feature or part of a CMOS substrate (e.g., a photodiode for sensing emitted photons and converting them to electrical current).

Methods of Modulating Surface Density of Immobilized Nucleic Acids

An aspect of the present disclosure provides for methods of controlling the density of immobilized nucleic acids on a substrate surface (e.g., a surface density) by controlling the silanation process. A "surface density" as used herein refers to the number of immobilized molecular structures (e.g., silanes, nucleic acid constructs) per unit area distributed over specific coordinates of a surface. In some cases, surface density may be measured in an amount of molecules per unit area (e.g., pmoles/cm$^2$). In some cases, surface density may be measured in relative terms, for example by measuring properties of a surface with immobilized molecules such as kinetics of hybridization of an immobilized oligonucleotide with its complementary sequence as measured by quantities such as percent quenching (Pq), time of hybridization (t), area of quenching (Aq), and the like.

Example processes for controlling the density of nucleic acid constructs are illustrated in FIGS. 5A-D.

Figure 5A:
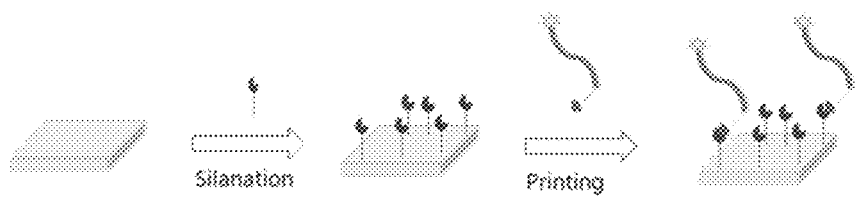
FIGS. 5A-5D show various methods for immobilizing a nucleic acid on a substrate at a target surface density.

As depicted in FIG. 5A, a first step may comprise immobilization of a silane comprising a first chemical group (depicted as a sector) present at a concentration X (e.g., as part of a CVD process or liquid deposition process as described above). After silanation, a nucleic acid or nucleic acids of interest optionally comprising fluorescent tag(s) are printed on the silanated surface as described above. The nucleic acid(s) may comprise a second chemical group (depicted as a wedge) such that upon contact with the first chemical group of the silanes, the two chemical groups react to form a covalent bond, thereby immobilizing the nucleic acid(s) on the surface.

Figure 5B:
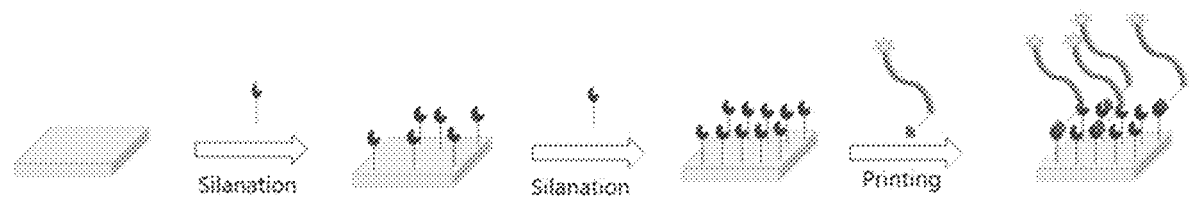

FIG. 5B shows another example of an immobilization process as described herein. As illustrated in FIG. 5B, a silanation step (e.g., CVD or liquid deposition) is performed multiple times, each time with the silane present at a concentration X. Additional silanations (e.g., 3, 4, 5, 6, 7, 8, 9, 10, or more) may be performed, as discussed above. The nucleic acid(s) of interest, optionally comprising fluorescent tags are printed on the silanated surface. The nucleic acid(s) may comprise a second chemical group (depicted as a wedge) such that upon contact with the first chemical group of the silanes, the two chemical groups react to form a covalent bond, thereby immobilizing the nucleic acid(s) on the surface. The resulting surface density of the nucleic acids may be higher than in the example illustrated in FIG. 5A.

Figure 5C:
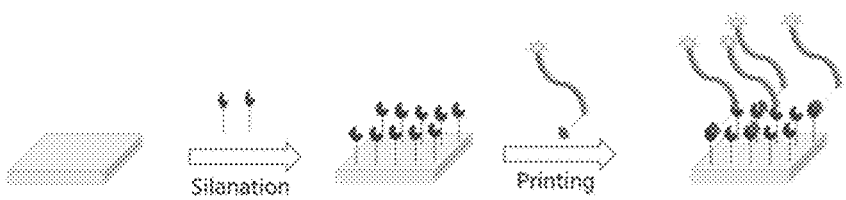

FIG. 5C illustrates a first step may comprise immobilization of a silane comprising a first chemical group (depicted as a sector) present at a concentration 2× (e.g., as part of a CVD process or liquid deposition process as described above). After silanation, a nucleic acid or nucleic acids of interest optionally comprising fluorescent tag(s) are printed on the silanated surface as described above. The nucleic acid(s) may comprise a second chemical group (depicted as a wedge) such that upon contact with the first chemical group of the silanes, the two chemical groups react to form a covalent bond, thereby immobilizing the nucleic acid(s) on the surface. The resulting surface density of the nucleic acids may be higher than in the example illustrated in FIG. 5A.

Figure 5D:
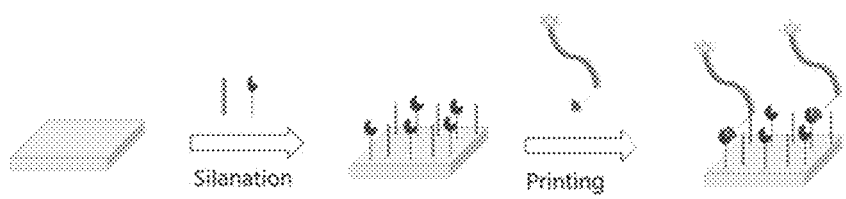

FIG. 5D illustrates a first step which comprises immobilizing two silanes on surface of a substrate, the first silane comprising a first reactive chemical group and a second silane lacking the first reactive chemical group. The second silane may comprise a second reactive chemical group or it may not. As illustrated in FIG. 5D, the two silanes may be present during the immobilization step at the same concentration (e.g., each at a concentration of X/2), though in general mixtures of silanes may be present in any ratio (e.g., a silane may comprise anywhere from about 1% or less to about 99% or more of a mixture of silanes). After silanation, a nucleic acid or nucleic acids of interest optionally comprising fluorescent tag(s) are printed on the silanated surface as described above. The nucleic acid(s) may comprise a third chemical group (depicted as a wedge) such that upon contact with the first silane comprising the first chemical group, the first and third chemical groups react to immobilize the nucleic acid construct(s) to the surface. Since the second silane does not comprise the first reactive chemical group, it is not expected to react with the nucleic acid construct(s).

Aside from those explicitly depicted in FIGS. 5A-D, still other silanation schemes are contemplated herein. For example, a silanation process which combines features of each of the examples illustrated in FIGS. 5A-D (e.g., comprising multiple rounds of silanation at various concentrations with some silanes comprising different reactive chemical groups or lacking them altogether) may be performed in order to achieve a target surface density of immobilized nucleic acid constructs.

Design and Synthesis of DBCO Modified Nucleic Acid Constructs

General synthetic routes leading to a strained cyclic alkyne group on a nucleic acid construct are available. See, for example, Scheme A.

Scheme A

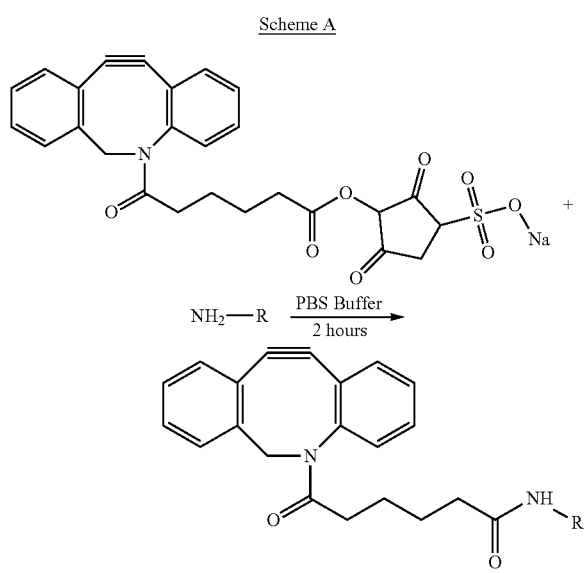

Reagents and conditions for Scheme A: oligonucleotide with free amino group, dibenzocyclooctyne-sulfo-N-hydroxysuccinimidyl ester, phosphate buffered saline (pH=7.2). NH$_2$—R in Scheme A is a nucleic acid construct (e.g., oligonucleotide) with or without protecting group(s), and a free amine. When NH$_2$—R comprises a nucleobase with protecting group(s), additional steps to add or remove the protecting group(s) may be added to the steps described in Scheme A.

Although the present disclosure presents a few synthetic routes leading to modified nucleic acid constructs, other similar or different synthetic routes may be possible when taking into consideration of the particular structure of the reactive chemical group added (e.g., substituted azide, substituted strained cyclic alkyne).

Labels & Dyes

A label or detectable label that is associated with nucleic acid constructs ad described herein may be any moiety that comprises one or more appropriate chemical substances or enzymes that directly or indirectly generate a detectable signal in a chemical, physical or enzymatic reaction. A large variety of labels are well known in the art. (See, for instance, PCT/GB2007/001770).

For instance, one class of such labels is fluorescent labels. Fluorescent labels have the advantage of coming in several different wavelengths (colors) allowing distinguishably labeling each different terminator molecule. (See, for example, Welch et al., *Chem. Eur. J.,* 5(3):951-960, 1999). One example of such labels is dansyl-functionalized fluorescent moieties. Another example is the fluorescent cyanine-based labels Cy3 and Cy5, which can also be used in the present disclosure. (See, Zhu et al., *Cytometry,* 28:206-211, 1997). Labels suitable for use are also disclosed in Prober et al., *Science,* 238:336-341, 1987; Connell et al., *BioTechniques,* 5(4):342-384, 1987; Ansorge et al., *Nucl. Acids Res.,* 15(11):4593-4602, 1987; and Smith et al., *Nature,* 321:674, 1986. Other commercially available fluorescent labels include, but are not limited to, fluorescein and related derivatives such as isothiocyanate derivatives, e.g. FITC and TRITC, rhodamine, including TMR, texas red and Rox, bodipy, acridine, coumarin, pyrene, benzanthracene, the cyanines, succinimidyl esters such as NHS-fluorescein, maleimide activated fluorophores such as fluorescein-5-maleimide, phosphoramidite reagents containing protected fluorescein, boron-dipyrromethene (BODIPY) dyes, and other fluorophores, e.g. 6-FAM phosphoramidite 2. All of these types of fluorescent labels may be used in combination, in mixtures and in groups, as desired and depending on the application.

Various commercially available fluorescent labels are known in the art, such as Alexa Fluor Dyes, e.g., Alexa 488, 555, 568, 660, 532, 647, and 700 (Invitrogen-Life Technologies, Inc., California, USA, available in a wide variety of wavelengths, see for instance, Panchuk, et al., *J. Hist. Cyto.,* 47:1179-1188, 1999). Also commercially available are a large group of fluorescent labels called ATTO dyes (available from ATTO-TEC GmbH in Siegen, Germany). These fluorescent labels may be used in combinations or mixtures to provide distinguishable emission patterns for all terminator molecules used in the assay since so many different absorbance and emission spectra are commercially available.

In various exemplary embodiments, a label comprises a fluorescent dye, such as, but not limited to, a rhodamine dye, e.g., R6G, R1 10, TAMRA, and ROX, a fluorescein dye, e.g., JOE, VIC, TET, HEX, FAM, etc., a halo-fluorescein dye, a cyanine dye. e.g., CY3, CY3.5, CY5, CY5.5, etc., a BODIPY® dye, e.g., FL, 530/550, TR, TMR, etc., a dichlororhodamine dye, an energy transfer dye, e.g., BIGD YE™ v 1 dyes, BIGD YE™ v 2 dyes, BIGD YE™ v 3 dyes, etc., Lucifer dyes, e.g., Lucifer yellow, etc., CASCADE BLUE®, Oregon Green, and the like. Other exemplary dyes are provided in Haugland, Molecular Probes Handbook of Fluorescent Probes and Research Products, Ninth Ed. (2003) and the updates thereto. Non-limiting exemplary labels also include, e.g., biotin, weakly fluorescent labels (see, for instance, Yin et al., *Appl Environ Microbiol.,* 69(7):3938, 2003; Babendure et al., *Anal. Biochem.,* 317(1):1, 2003; and Jankowiak et al., *Chem. Res. Toxicol.,* 16(3):304, 2003), non-fluorescent labels, colorimetric labels, chemiluminescent labels (see, Wilson et al., *Analyst,* 128(5):480, 2003; Roda et al., *Luminescence,* 18(2):72, 2003), Raman labels, electrochemical labels, bioluminescent labels (Kitayama et al., *Photochem. Photobiol.,* 77(3):333, 2003; Arakawa et al., *Anal. Biochem.,* 314(2):206, 2003; and Maeda, *J. Pharm. Biomed. Anal.,* 30(6): 1725, 2003), and the like.

Multiple labels can also be used in the disclosure. For example, bi-fluorophore FRET cassettes (*Tet. Letts.,* 46:8867-8871, 2000) are well known in the art and can be utilized in the disclosed methods. Multi-fluor dendrimeric systems (*J. Amer. Chem. Soc.,* 123:8101-8108, 2001) can also be used. Other forms of detectable labels are also available. For example, microparticles, including quantum dots (Empodocles, et al., *Nature,* 399:126-130, 1999), gold nanoparticles (Reichert et al., *Anal. Chem.,* 72:6025-6029, 2000), microbeads (Lacoste et al., *Proc. Natl. Acad. Sci. USA,* 97(17):9461-9466, 2000), and tags detectable by mass spectrometry can all be used.

Multi-component labels can also be used in the disclosure. A multi-component label is one which is dependent on the interaction with a further compound for detection. The most common multi-component label used in biology is the biotin-streptavidin system. Biotin is used as the label attached to the nucleotide base. Streptavidin is then added separately to enable detection to occur. Other multi-component systems are available. For example, dinitrophenol has a commercially available fluorescent antibody that can be used for detection.

Thus, a "label" as presently defined is a moiety that facilitates detection of a molecule. Common labels in the context of the present disclosure include fluorescent, luminescent, light-scattering, and/or colorimetric labels. Suitable labels may also include radionuclides, substrates, cofactors, inhibitors, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. As other non-limiting examples, the label can be a luminescent label, a light-scattering label (e.g., colloidal gold particles), or an enzyme (e.g., Horse Radish Peroxidase (HRP)).

Fluorescence energy transfer (FRET) dyes may also be employed, such as DY-630/DY-675 from Dyomics GmbH of Germany, which also commercially supplies many different types of dyes including enzyme-based labels, fluorescent labels, etc. (See, for instance, Dohm et al., "Substantial biases in ultra-short read data sets from high-throughput DNA sequencing," *Nucleic Acids Res.,* 36:e105, 2008). Other donor/acceptor FRET labels include, but are not limited to:

| Donor | Acceptor | $R_0$ (Å) |
| --- | --- | --- |
| Fluorescein | Tetramethylrhodamine | 55 |
| IAEDANS | Fluorescein | 46 |
| EDANS | Dabcyl | 33 |
| Fluorescein | Fluorescein | 44 |
| BODIPY FL | BODIPY FL | 57 |
| Fluorescein | QSY 7 and QSY 9 dyes | 61 |

(See also, Johansen, M. K., "Choosing Reporter-Quencher Pairs for Efficient Quenching Through Formation of Intramolecular Dimers," Methods in Molecular Biology, vol. 335: Fluorescent Energy Transfer Nucleic Acid Probes: Designs and Protocols, Edited by: V. V. Didenko, Humana Press Inc., Totowa, N.J.). Other dye quenchers are commercially available, including dabcyl, QSY quenchers and the like. (See also, Black Hole Quencher Dyes from Biosearch Technologies, Inc., Novato, Calif.; Iowa Black Dark Quenchers from Integrated DNA Technologies, Inc. of Coralville, Iowa; and other dye quenchers sold by Santa Cruz Biotechnology, Inc. of Dallas, Tex.).

The label and linker construct can be of a size or structure sufficient to act as a block to the incorporation of a further nucleotide onto the nucleotide of the disclosure. This permits controlled polymerization to be carried out. The block can be due to steric hindrance, or can be due to a combination of size, charge and structure.

The terminology used herein is for the purpose of describing particular cases only and is not intended to be limiting. As used herein, the singular forms "a", "an" and "the" can be intended to include the plural forms as well, unless the context clearly indicates otherwise. Furthermore, to the extent that the terms "including", "includes", "having", "has", "with", or variants thereof can be used in either the detailed description and/or the claims, such terms can be intended to be inclusive in a manner similar to the term "comprising".

The term "about" or "approximately" can mean within an acceptable error range for the particular value as determined by one of ordinary skill in the art, which may depend in part on how the value is measured or determined, i.e., the limitations of the measurement system. For example, the term "about" as used herein indicates the value of a given quantity varies by +/−10% of the value, or optionally +/−5% of the value, or in some embodiments, by +/−1% of the value so described. Alternatively, "about" can mean a range of up to 20%, up to 10%, up to 5%, or up to 1% of a given value. Alternatively, particularly with respect to biological systems or processes, the term can mean within an order of magnitude, within 5-fold, or within 2-fold, of a value. Where particular values may be described in the application and claims, unless otherwise stated the term "about" meaning within an acceptable error range for the particular value should be assumed. Also, where ranges and/or subranges of values are provided, the ranges and/or subranges can include the endpoints of the ranges and/or subranges.

The term "substantially" as used herein can refer to a value approaching 100% of a given value. For example, an active agent that is "substantially localized" in an organ can indicate that about 90% by weight of an active agent, salt, or metabolite can be present in an organ relative to a total amount of an active agent, salt, or metabolite. In some cases, the term can refer to an amount that can be at least about 90%, 91%, 92%, 93%, 94%, 95%, 96%, 97%, 98%, 99%, 99.9%, or 99.99% of a total amount. In some cases, the term can refer to an amount that can be about 100% of a total amount.

As used herein, nucleotides are abbreviated with 3 letters. The first letter indicates the identity of the nitrogenous base (e.g. A for adenine, G for guanine), the second letter indicates the number of phosphates (mono, di, tri), and the third letter is P, standing for phosphate. Nucleoside triphosphates that contain ribose as the sugar, ribonucleoside triphosphates, are conventionally abbreviated as NTPs, while nucleoside triphosphates containing deoxyribose as the sugar, deoxyribonucleoside triphosphates, are abbreviated as dNTPs. For example, dATP stands for deoxyribose adenine triphosphate. NTPs are the building blocks of RNA, and dNTPs are the building blocks of DNA.

The term "immobilization" as used herein generally refers to forming a covalent bond between two reactive groups. For example, polymerization of reactive groups is a form of immobilization. A Carbon to Carbon covalent bond formation is an example of immobilization.

The term "label" or "detectable label" as used herein generally refers to any moiety or property that is detectable, or allows the detection of an entity which is associated with the label. For example, a nucleotide, oligo- or polynucleotide that comprises a fluorescent label may be detectable. In some cases, a labeled oligo- or polynucleotide permits the detection of a hybridization complex, for example, after a labeled nucleotide has been incorporated by enzymatic means into the hybridization complex of a primer and a template nucleic acid. A label may be attached covalently or non-covalently to a nucleotide, oligo- or polynucleotide. In some cases, a label can, alternatively or in combination: (i) provide a detectable signal; (ii) interact with a second label to modify the detectable signal provided by the second label, e.g., FRET; (iii) stabilize hybridization, e.g., duplex formation; (iv) confer a capture function, e.g., hydrophobic affinity, antibody/antigen, ionic complexation, or (v) change a physical property, such as electrophoretic mobility, hydrophobicity, hydrophilicity, solubility, or chromatographic behavior. Labels may vary widely in their structures and their mechanisms of action. Examples of labels may include, but are not limited to, fluorescent labels, non-fluorescent labels, colorimetric labels, chemiluminescent labels, bioluminescent labels, radioactive labels, mass-modifying groups, antibodies, antigens, biotin, haptens, enzymes (including, e.g., peroxidase, phosphatase, etc.), and the like. Fluorescent labels may include dyes of the fluorescein family, dyes of the rhodamine family, dyes of the cyanine family, or a coumarine, an oxazine, a boradiazaindacene or any derivative thereof. Dyes of the fluorescein family include, e.g., FAM, HEX, TET, JOE, NAN and ZOE. Dyes of the rhodamine family include, e.g., Texas Red, ROX, R110, R6G, and TAMRA. FAM, HEX, TET, JOE, NAN, ZOE, ROX, R110, R6G, and TAMRA are commercially available from, e.g., Perkin-Elmer, Inc. (Wellesley, Mass., USA), Texas Red is commercially available from, e.g., Thermo Fisher Scientific, Inc. (Grand Island, N.Y., USA). Dyes of the cyanine family include, e.g., CY2, CY3, CY5, CY5.5 and CY7, and are commercially available from, e.g., GE Healthcare Life Sciences (Piscataway, N.J., USA).

The term "different detectable label" or "differently labeled" as used herein generally refers to the detectable label being a different chemical entity or being differentiated among the different bases to which the labels are attached to.

As used herein, the solid substrate used can be biological, non-biological, organic, inorganic, or a combination of any of these. The substrate can exist as one or more particles, strands, precipitates, gels, sheets, tubing, spheres, containers, capillaries, pads, slices, films, plates, slides, or semiconductor integrated chips, for example. The solid substrate can be flat or can take on alternative surface configurations. For example, the solid substrate can contain raised or depressed regions on which synthesis or deposition takes place. In some examples, the solid substrate can be chosen to provide appropriate light-absorbing characteristics. For example, the substrate can be a polymerized Langmuir Blodgett film, functionalized glass (e.g., controlled pore glass), silica, titanium oxide, aluminum oxide, indium tin oxide (ITO), Si, Ge, GaAs, GaP, $SiO_2$, $SiN_4$, modified silicon, the top dielectric layer of a semiconductor integrated circuit (IC) chip, such as a complementary metal-oxide-semiconductor (CMOS) IC, or any one of a variety of gels or polymers such as (poly)tetrafluoroethylene, (poly)vinylidenedifluoride, polystyrene, polycarbonate, polydimethylsiloxane (PDMS), polymethylmethacrylate (PMMA), polycyclic olefins, or combinations thereof.

Solid substrates can comprise polymer coatings or gels, such as a polyacrylamide gel or a PDMS gel. Gels and coatings can additionally comprise components to modify their physicochemical properties, for example, hydrophobicity. For example, a polyacrylamide gel or coating can comprise modified acrylamide monomers in its polymer structure such as ethoxylated acrylamide monomers, phosphorylcholine acrylamide monomers, betaine acrylamide monomers, and combinations thereof.

The term "hydroxyl protective group" as used herein generally refers to any group which forms a derivative of the hydroxyl group that is stable to the projected reactions wherein said hydroxyl protective group subsequently optionally can be selectively removed. Said hydroxyl derivative can be obtained by selective reaction of a hydroxyl protecting agent with a hydroxyl group.

The term "complementary" as used herein in reference to polynucleotides generally refers to a polynucleotide that forms a stable duplex with its "complement," e.g., under relevant assay conditions. Typically, two polynucleotide sequences that are complementary to each other have mismatches at less than about 20% of the bases, at less than about 10% of the bases, preferably at less than about 5% of the bases, and more preferably have no mismatches.

A "polynucleotide sequence" or "nucleotide sequence" as used herein generally refers to a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

A "sugar moiety" as used herein generally refers to both ribose and deoxyribose and their derivatives/analogs.

Two polynucleotides "hybridize" when they associate to form a stable duplex, e.g., under relevant assay conditions. Nucleic acids hybridize due to a variety of well characterized physicochemical forces, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, New York), as well as in Ausubel, infra.

The term "polynucleotide" (and the equivalent term "nucleic acid" or "nucleic acid construct") encompasses any physical string of monomer units that can be corresponded to a string of nucleotides, including a polymer of nucleotides, e.g., a typical DNA or RNA polymer, peptide nucleic acids (PNAs), modified oligonucleotides, e.g., oligonucleotides comprising nucleotides that are not typical to biological RNA or DNA, such as 2'-O-methylated oligonucleotides, and the like. The nucleotides of the polynucleotide can be deoxyribonucleotides, ribonucleotides or nucleotide analogs, can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like. The polynucleotide can additionally comprise non-nucleotide elements such as labels, quenchers, blocking groups, or the like. The polynucleotide can be, e.g., single-stranded or double-stranded.

The term "oligonucleotide" as used herein generally refers to a nucleotide chain. In some cases, an oligonucleotide is less than 200 residues long, e.g., between 15 and 100 nucleotides long. The oligonucleotide can comprise at least or about 1, 2, 3, 4, 5, 6, 7, 8, 9, 10, 15, 20, 25, 30, 35, 40, 45, or 50 bases. The oligonucleotides can be from about 3 to about 5 bases, from about 1 to about 50 bases, from about 8 to about 12 bases, from about 15 to about 25 bases, from about 25 to about 35 bases, from about 35 to about 45 bases, or from about 45 to about 55 bases. The oligonucleotide (also referred to as "oligo") can be any type of oligonucleotide (e.g., a primer). Oligonucleotides can comprise natural nucleotides, non-natural nucleotides, or combinations thereof.

The term "analog" in the context of nucleic acid analog is meant to denote any of a number of known nucleic acid analogs such as, but not limited to, LNA, PNA, etc. Further, a "nucleoside triphosphate analog" may contain 3-7 phosphate groups, wherein one of the oxygen (—$O^-$) on the phosphate may be replaced with sulfur (—$S^-$) or borane (—$BH_3^-$). Still further, a "nucleoside triphosphate analog" may contain a base which is an analog of adenine (A), guanine (G), thymine (T), cytosine (C) and uracil (U). For example, the bases are included:

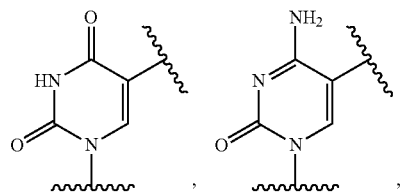

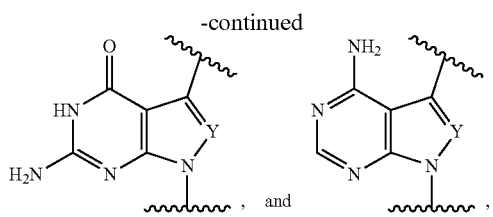

wherein Y is CH or N. One nitrogen atom of the purines and pyrimidines base, or analogs thereof, is connected to the ribose or deoxyribose C-1 position. As shown above, one carbon atom of the purines and pyrimidines base, or analogs thereof, is connected to a linker to a label.

The term "aromatic" used in the present application means an aromatic group which has at least one ring having a conjugated pi electron system, i.e., aromatic carbon molecules having 4n+2 delocalized electrons, according to Hickeys rule, and includes both carbocyclic aryl, e.g., phenyl, and heterocyclic aryl groups, e.g., pyridine. The term includes monocyclic or fused-ring polycyclic, i.e., rings which share adjacent pairs of carbon atoms, groups.

The term "heterocyclic nucleic acid base" used herein means the nitrogenous bases of DNA or RNA. These bases can be divided into two classes: purines and pyrimidines. The former includes guanine and adenine and the latter includes cytosine, thymine, and uracil.

The term "aromatic" when used in the context of "aromatic solvent" as used in the present disclosure means any of the known and/or commercially available aromatic solvents, such as, but not limited to, toluene, benzene, xylenes, any of the Kesols, and/or GaroSOLs, and derivatives and mixtures thereof.

The term "alkyl," by itself or as part of another substituent means, unless otherwise stated, a straight or branched chain, or cyclic hydrocarbon radical, or combination thereof, which may be fully saturated, mono- or polyunsaturated and can include di- and multivalent radicals, having the number of carbon atoms designated, i.e. $C_1$-$C_{10}$ means one to ten carbon atoms in a chain. Non-limiting examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl."

The term "alkylene" by itself or as part of another substituent means a divalent radical derived from an alkane, as exemplified, but not limited to, by —$CH_2CH_2CH_2CH_2$—, and further includes those groups described below as "heteroalkylene." Typically, an alkyl (or alkylene) group may have from 1 to 24 carbon atoms, with those groups having 10 or fewer carbon atoms being preferred in the present disclosure. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_2$, —$CH_2$—$CH_2$—S(O)$_2$—$CH_3$, —CHCH—O—$CH_3$, —Si($CH_3$)$_3$, —$CH_2$—CHN—OCH$_3$, and —CHCH—N($CH_3$)—$CH_3$. Up to two heteroatoms may be consecutive, such as, for example, —$CH_2$—NH—OCH$_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini, e.g., alkyleneoxy, alkylenedioxy, alkyleneamino, alkylenediamino, and the like. Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl," by themselves or in combination with other terms, represent, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring, such as those that follow Hückel's rule (4n+2, where n is any integer), or multiple rings (preferably from 1 to 5 rings), which are fused together or linked covalently and including those which obey Clar's Rule. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms, e.g., aryloxy, arylthioxy, arylalkyl, includes both aryl and heteroaryl rings as defined above. Thus, the term "arylalkyl" is meant to include those radicals in which an aryl group is attached to an alkyl group, e.g., benzyl, phenethyl, pyridylmethyl and the like, including those alkyl groups in which a carbon atom, e.g., a methylene group, has been replaced by, for example, an oxygen atom, e.g., phenoxymethyl, 2-pyridyloxymethyl, 3-(1-naphthyloxy)propyl, and the like.

Each of the above terms, e.g., "alkyl," "heteroalkyl," "aryl" and "heteroaryl," is meant to include both substituted and unsubstituted forms of the indicated radical. Preferred substituents for each type of radical are provided below.

Substituents for the alkyl and heteroalkyl radicals, including those groups often referred to as alkylene, alkenyl, heteroalkylene, heteroalkenyl, alkynyl, cycloalkyl, heterocycloalkyl, cycloalkenyl, and heterocycloalkenyl, are generically referred to as "alkyl group substituents," and they can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2M'+1), where M' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the disclosure includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, the term "alkyl" is meant to include groups including carbon atoms bound to groups other than hydrogen groups, such as haloalkyl, e.g., —CF$_3$ and —CH$_2$CF$_3$) and acyl, e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R"', —OC(O)W, —C(O)R', —CO$_2$R', —CONR'R", —OC(O)NR'R", —NR"C(O)R', —NR'—C(O)NR"R"', —NR" C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the disclosure includes more than one R group, for example, each of the R groups is independently selected as are each R', R", R"' and R"" groups when more than one of these groups is present. In the schemes that follow, the symbol X represents "R" as described above.

As used herein, the term "click chemistry," generally refers to reactions that are modular, wide in scope, give high yields, generate only inoffensive byproducts, such as those that can be removed by nonchromatographic methods, and are stereospecific (but not necessarily enantioselective). See, e.g., Angew. Chem. Int. Ed., 2001, 40(11):2004-2021, which is entirely incorporated herein by reference for all purposes. In some cases, click chemistry can describe a pair of functional groups that can selectively react with each other in mild, aqueous conditions.

An example of click chemistry reaction can be the Huisgen 1,3-dipolar cycloaddition of an azide and an alkyne, or a Copper-catalyzed reaction of an azide with an alkyne, to form a 5-membered heteroatom ring called 1,2,3-triazole. The reaction can also be known as a Cu(I)-Catalyzed Azide-Alkyne Cycloaddition (CuAAC), a Cu(I) click chemistry or a Cu$^+$ click chemistry. Catalyst for the click chemistry can be Cu(I) salts, or Cu(I) salts made in situ by reducing Cu(II) reagent to Cu(I) reagent with a reducing reagent (Pharm Res. 2008, 25(10): 2216-2230). Known Cu(II) reagents for the click chemistry can include, but are not limited to, Cu(II)-(TBTA) complex and Cu(II) (THPTA) complex. TBTA, which is tris-[(1-benzyl-1H-1,2,3-triazol-4-yl)methyl]amine, also known as tris-(benzyltriazolylmethyl)amine, can be a stabilizing ligand for Cu(I) salts. THPTA, which is tris-(hydroxypropyltriazolylmethyl) amine, can be another example of stabilizing agent for Cu(I). Other conditions can also be accomplished to construct the 1,2,3-triazole ring from an azide and an alkyne using copper-free click chemistry, such as by the Strain-promoted Azide-Alkyne Click chemistry reaction (SPAAC, see, e.g., Chem. Commun., 2011, 47:6257-6259 and Nature, 2015, 519 (7544):486-90), each of which is entirely incorporated herein by reference for all purposes.

Unless otherwise noted, the term "catalytic amount," as used herein, includes that amount of the reactant that is sufficient for a reaction of the process of the disclosure to occur. Accordingly, the quantity that constitutes a catalytic amount is any quantity that serves to allow or to increase the rate of reaction, with larger quantities typically providing a greater increase. The quantity used in any particular application may be determined in large part by the individual needs of the manufacturing facility. Factors which enter into such a determination include the catalyst cost, recovery costs, desired reaction time, and system capacity. An amount of reactant may be used in the range from about 0.001 to about 0.5 equivalents, from about 0.001 to about 0.25 equivalents, from about 0.01 to about 0.25 equivalents, from about 0.001 to about 0.1, from about 0.01 to about 0.1 equivalents, including about 0.005, about 0.05 or about 0.08 equivalents of the reactant/substrate, or in the range from about 0.001 to about 1 equivalents, from about 0.001 to about 0.5 equivalents, from about 0.001 to about 0.25 equivalents, from about 0.001 to about 0.1 equivalents, from about 0.01 to about 0.5 equivalents or from about 0.05 to about 0.1 equivalents, including about 0.005, about 0.02 or about 0.04 equivalents.

Applicants are aware that there are many conventions and systems by which organic compounds may be named and otherwise described, including common names as well as systems, such as the IUPAC system.

Synthetic Methods

The size and scale of the synthetic methods may vary depending on the desired amount of end product. It is understood that while specific reactants and amounts are provided in the Examples, one of skill in the art knows other alternative and equally feasible sets of reactants that may also yield the same compounds. Thus, where general oxidizers, reducers, solvents of various nature (aprotic, apolar, polar, etc.) are utilized, equivalents may be contemplated for use in the present methods.

For instance, in all instances, where a drying agent is used, contemplated drying agents include all those reported in the literature and known to one of skill, such as, but not limited to, magnesium sulfate, sodium sulfate, calcium sulfate, calcium chloride, potassium chloride, potassium hydroxide, sulfuric acid, quicklime, phosphorous pentoxide, potassium carbonate, sodium, silica gel, aluminum oxide, calcium hydride, lithium aluminum hydride (LAH), potassium hydroxide, and the like. (See, Burfield et al., "Desiccant Efficiency in Solvent Drying. A Reappraisal by Application of a Novel Method for Solvent Water Assay," *J. Org. Chem.*, 42(18):3060-3065, 1977). The amount of drying agent to add in each work up may be optimized by one of skill in the art and is not particularly limited. Further, although general guidance is provided for work-up of the intermediates in each step, it is generally understood by one of skill that other optional solvents and reagents may be equally substituted during the work-up steps. However, in some exceptional instances, it was found the very specific work-up conditions are required to maintain an unstable intermediate. Those instances are indicated below in the steps in which they occur.

Steps below may indicate various work-ups following termination of the reaction. A work-up involves generally quenching of a reaction to terminate any remaining catalytic activity and starting reagents. This is generally followed by addition of an organic solvent and separation of the aqueous layer from the organic layer. The product is typically obtained from the organic layer and unused reactants and other spurious side products and unwanted chemicals are generally trapped in the aqueous layer and discarded. The work-up in standard organic synthetic procedures found throughout the literature is generally followed by drying the product by exposure to a drying agent to remove any excess water or aqueous byproducts remaining partially dissolved in the organic layer and concentration of the remaining organic layer. Concentration of product dissolved in solvent may be achieved by any known means, such as evaporation under pressure, evaporation under increased temperature and pressure, and the like. Such concentrating may be achieved by use of standard laboratory equipment such as rotary-evaporator distillation, and the like. This is optionally followed by one or more purification steps which may include, but is not limited to, flash column chromatography, filtration through various media and/or other preparative methods known in the art and/or crystallization/recrystallization. (See, for instance, Addison Ault, "Techniques and Experiments for Organic Chemistry," 6$^{th}$ Ed., University Science Books, Sausalito, Calif., 1998, Ann B. McGuire, Ed., pp. 45-59). Though certain organic co-solvents and quenching agents may be indicated in the steps described below, other equivalent organic solvents and quenching agents known to one of skill may be employed equally as well and are fully contemplated herein. Further, most of the work-ups in most steps may be further altered according to preference and desired end use or end product. Drying and evaporation, routine steps at the organic synthetic chemist bench, need not be employed and may be considered in all steps to be optional. The number of extractions with organic solvent may be as many as one, two, three, four, five, or ten or more, depending on the desired result and scale of reaction. Except where specifically noted, the volume, amount of quenching agent, and volume of organic solvents used in the work-up may be varied depending on specific reaction conditions and optimized to yield the best results.

Additionally, where inert gas or noble gas is indicated, any inert gas commonly used in the art may be substituted for the indicated inert gas, such as argon, nitrogen, helium, neon, etc.

A number of patents and publications are cited herein in order to more fully describe and disclose the present methods, compounds, compositions and kits, and the state of the art to which they pertain. The references, publications, patents, books, manuals and other materials cited herein to illuminate the background, known methods, and in particular, to provide additional details with respect to the practice of the present methods, compositions and/or kits, are all incorporated herein by reference in their entirety for all purposes, to the same extent as if each individual reference was specifically and individually indicated to be incorporated by reference.

EXAMPLES

It is understood that the examples and embodiments described herein are for illustrative purposes and that various modifications or changes in light thereof may be suggested to persons skilled in the art and are to be included within the spirit and purview of this application and scope of the claims. Accordingly, the following examples are offered to illustrate, but not to limit, the claimed invention.

Example 1: Functionalization of CMOS Surface with Azide Modified Silane and Immobilization of DBCO Functionalized Oligonucleotides A substrate comprises a CMOS wafer or part of it (die or chip). The CMOS surface is functionalized with an azidosilane (e.g., 3-Azidopropyltriethoxysilane). The deposition is performed in vapor phase (e.g., by CVD). The CMOS surface is heated within a reduced pressure environment (e.g., 1-3 torr) at an elevated temperature (e.g., 120° C.) in the presence of 3-azidopropyltriethoxysilane. The exposure of the CMOS surface to the silane is done from 1 to n times, until the desired density of azide coating on the surface is achieved.

The azide functionalized surface is then exposed to oligonucleotides functionalized with strained cyclic alkynes (e.g., dibenzocyclooctyne (DBCO), 10-(6-oxo (dibenzo[b,f] azacyclooct-4-yn-1-yl)-capramido-N-ethyl)-O-triethyleneglycol (DBCO-TEG)) and allowed to react at room temperature and neutral pH. The oligonucleotide may be diluted into a printing solution and the solution dispensed with a non-contact method on a given feature of the CMOS, such as a photodiode for sensing photons emitted and transforming sensed photons into a measurable electrical current.

After a short incubation at room temperature, the surface is washed with a 0.2% solution of SDS (Sodium Dodecyl Sulfate) in water and dried. At this point the oligonucleotides chains are covalently immobilized on the surface and excess unreacted material has been washed off.

The CMOS surface is now active and can be used as a sensor for the detection of complementary probes, PCR amplification and detection of the amplicons generated, detection of primers depleted and the relative controls, and the like.

Example 2: Immobilization of DBCO Modified Silanes on CMOS Surface and Immobilization of Azido Functionalized Oligonucleotides A substrate comprises a CMOS wafer or part of it (die or chip). The CMOS surface is functionalized with a silane modified with a strained cyclic alkyne (e.g., with Dibenzocyclooctyne-Polyethyleneglycol-Silane (DBCO-PEG-silane)). The deposition is performed in liquid phase. The exposure of the CMOS surface to the silane is done from 1 to n times, until the desired level of density of azide coating is achieved.

The azide functionalized surface is then exposed to oligonucleotides functionalized with an azido moiety and allowed to react at room temperature and neutral pH.

The oligonucleotide may be diluted into a printing solution and the solution dispensed with a non-contact method, with high precision, on a given feature of the CMOS, for instance a photodiode for sensing photons emitted and transforming it into a measurable electrical current.

After a short incubation at room temperature, the surface is washed with a 0.2% solution of SDS (Sodium Dodecyl Sulfate) in water, and dried. At this point the oligonucleotides chains are covalently immobilized on the surface and excess unreacted material has been washed off.

The CMOS surface is now active and can be used as a sensor for the detection of complementary probes, PCR amplification and detection of the amplicons generated, detection of primers depleted and the relative controls, and the like.

Example 3: Modulation of Density of Immobilized Oligonucleotides on CMOS Surface by Controlling the Printing Concentration A functionalized CMOS surface is prepared according to Example 1 or 2. The dispensing of the modified oligonucleotide is modulated by controlling the concentration of the nucleic acid target(s) (e.g., oligonucleotide(s)) in a printing buffer. The concentration of the oligonucleotide in the printing buffer is modulated from 1 to 25 µM to achieve different amount of oligonucleotide immobilized onto the CMOS surface.

The properties of the oligonucleotides immobilized on the surface according to this embodiment vary according to the conditions used. Properties include but are not limited to kinetics of hybridization of the oligonucleotide with the amplicons generated, primers depleted and the relative controls, such as Percent Quenching (Pq), Time of hybridization (t), Area of quenching (Aq), etc.

Figure 10A:
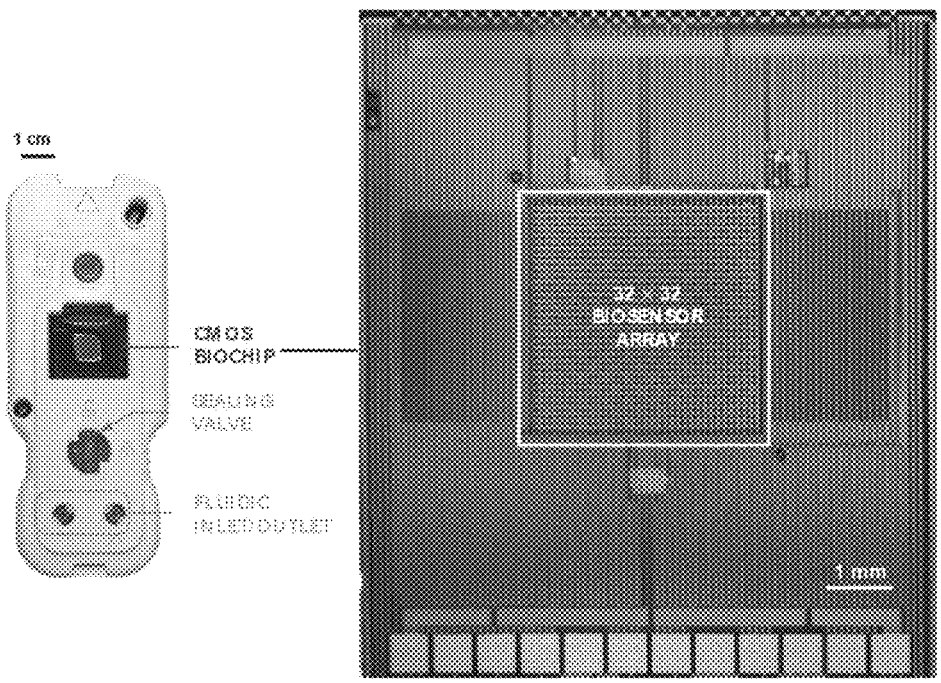
FIGS. 10A and 10B illustrate a CMOS biochip and a biosensing pixel, respectively.
Figure 10B:
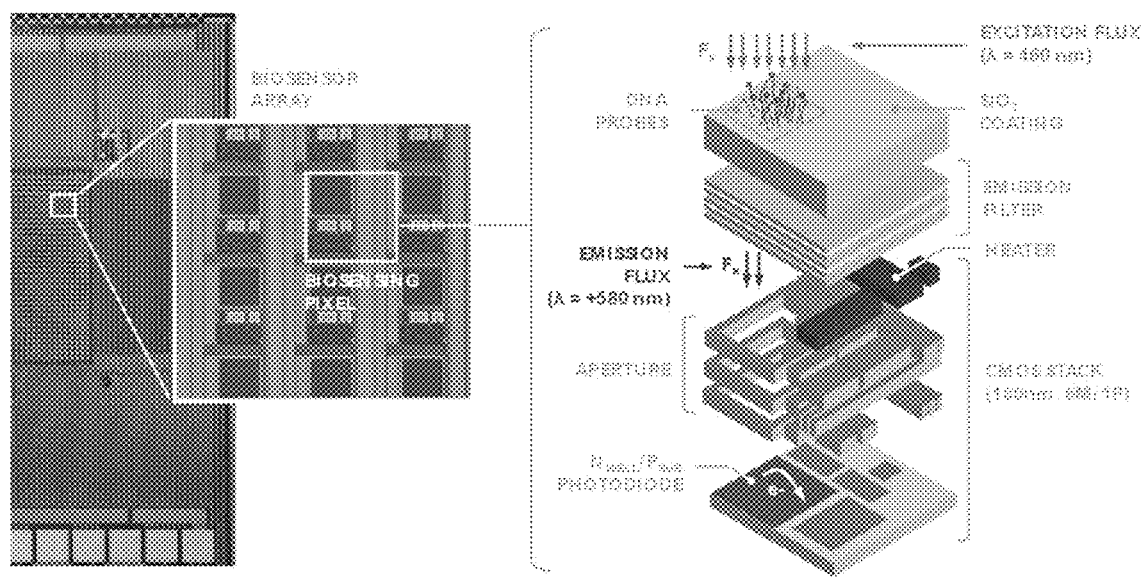

The experiments are conducted using a cartridge as shown in FIG. 10A which includes a CMOS Biochip and a fluidic cap with an inlet and outlet and a sealing valve. The cartridge accepts 50 µL of input volume and can withstand PCR cycling conditions. The CMOS biochip includes an integrated array of 1024 biosensing pixels. The cross-section of the pixel is shown in FIG. 10B. Each pixel includes a 60 µm×60 µm photodiode along with the integrated sigma-delta detection circuitry. The biochip also includes a heater, which is uniformly spread out across the entire biochip, and an integrated emission filter that blocks the excitation light from the light source and passes the emission light from the fluorophore, enabling fluorescence detection. DNA probes are immobilized on the top $SiO_2$ surface using protocols described herein. Different pixels can have different probes immobilized on them permitting multiplexed DNA detection.

Figure 11A:
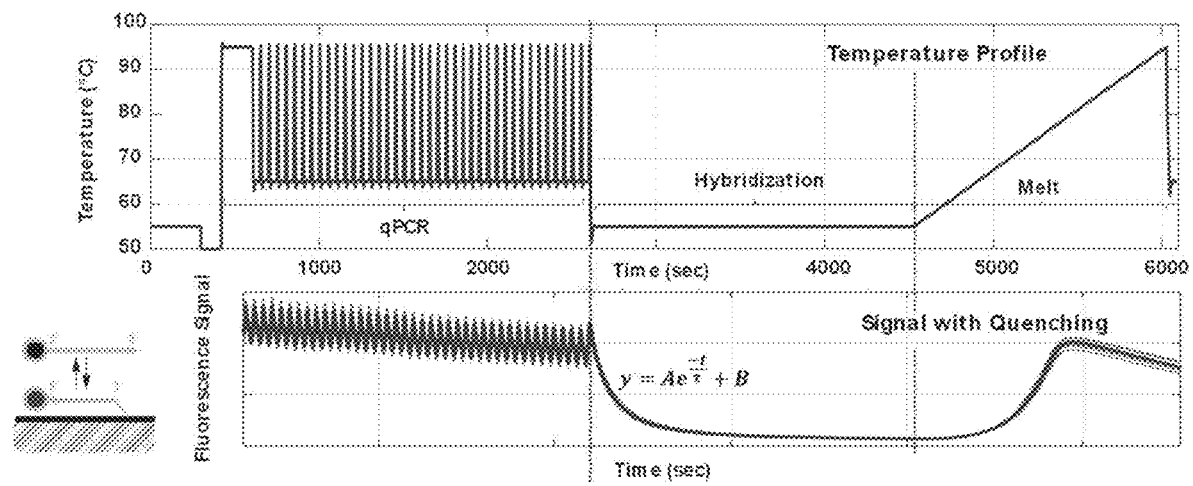
FIG. 11A depicts a temperature profile and corresponding fluorescence profile for an experiment performed on a biochip.
Figure 11B:
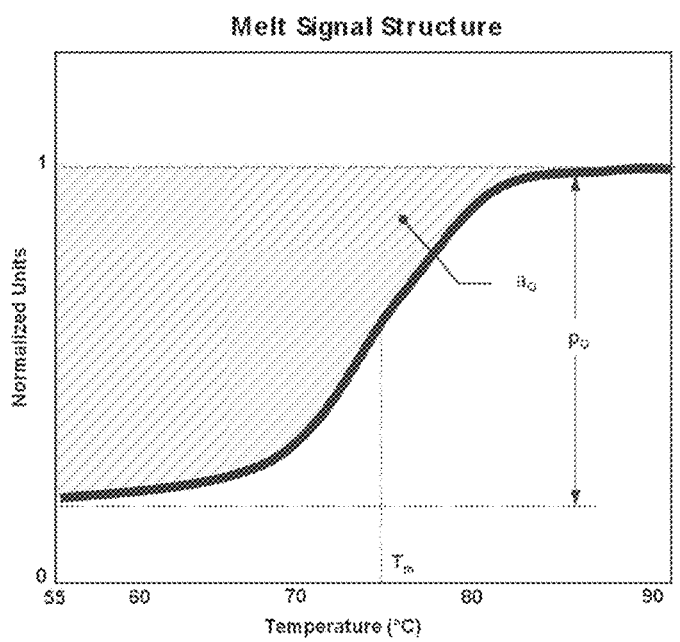
FIG. 11B shows a corresponding representative melt curve.

The experiments are run using the temperature profile as shown in FIG. 11A which includes (i) a quantitative PCR cycling (qPCR) phase; (ii) a hybridization phase; and (iii) a melt phase. Images are collected using the CMOS biochip during all the 3 phases. The qPCR phase has 40 cycles of denaturation step at 95° C. and annealing at 65° C. and is used to amplify the sample. During the hybridization phase, the temperature is held constant at 55° C. for 30 minutes. During this phase, quencher labelled targets bind to the fluorescently labelled probes creating a drop in signal. The kinetics of hybridization can be modeled using a first-order kinetics equation and has a characteristic time constant, tau ($\tau$). During the melt phase, the temperature is slowly ramped up from 55° C. to 95° C. in 25 minutes to perform high resolution melt (HRM) analysis. During this phase, the hybridized target comes off the probes causing an increase in signal. At higher temperatures, signal drops due to the dependence of fluorescence on temperature. The melt curves are "conditioned" to correct for the temperature dependence of fluorescence and then normalized between 0 and 1 as shown in FIG. 11B.

Three metrics are extracted from melt curves (i) Percentage Quenching (Pq) at the initial hybridization temperature; (ii) area of quenching (Aq), which refers to the area under the curve as shown by the shaded section; and (iii) mid-point melting temperature (Tm) which refers to the temperature at the curve reaches 50% point. These three metrics along with the hybridization time constant (tau) is used to characterize the binding of the quencher labelled target to the fluorescently labeled probe.

Example 4: Modulation of Density of Immobilized Oligonucleotides on CMOS Surface by Controlling the Printing Concentration Functionalized CMOS surfaces were prepared according to Example 1 comprising four different oligonucleotides probes (HybC1, HybC2, HybC1-TEG, NP) The concentration of each oligonucleotide in its printing buffer (300 mM sodium phosphate) was modulated from 1 to 25 µM (e.g., 6.3 µM, 8.3 µM, 12.5 µM, 25 µM; each 20 µL solution) to achieve different amounts of oligonucleotide immobilized onto the CMOS surface. Probes were printed onto the array surface with a liquid handling system. After a short incubation at room temperature, the surface was washed with a 0.2% solution of SDS in water and dried.

Figure 6:
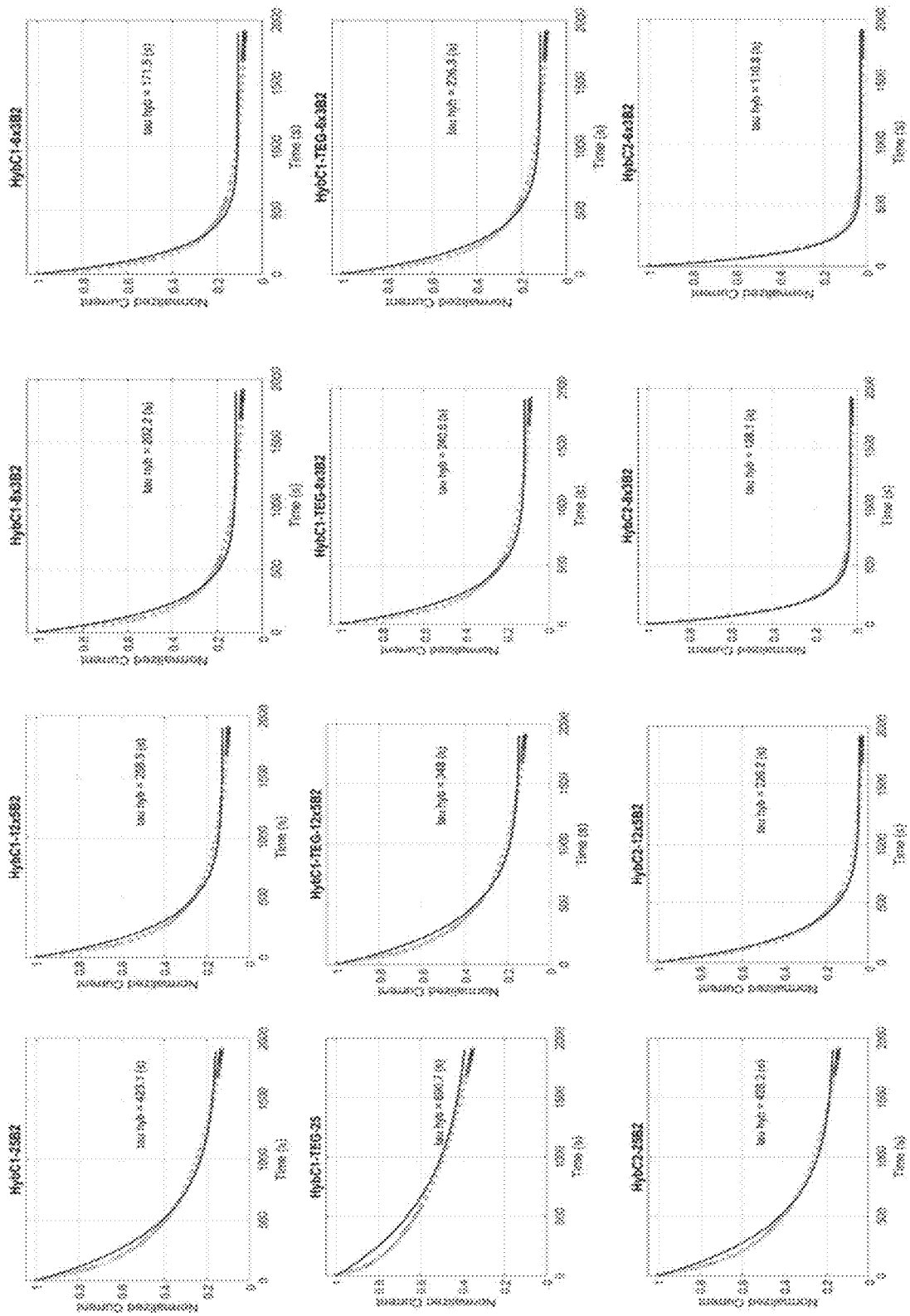
FIG. 6 shows kinetic measurements of an immobilized oligonucleotide hybridizing its target.
Figure 7:
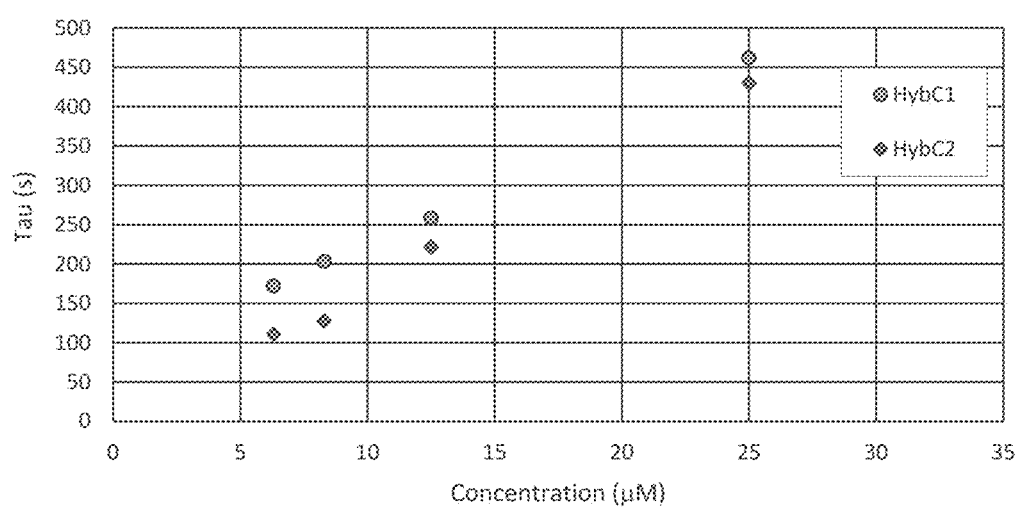
FIG. 7 shows a graph of time of hybridization as a function of printing concentration of a nucleic acid molecule.

The kinetics of hybridization of the immobilized oligonucleotides with their corresponding complementary target nucleotides at the same concentration was measured and characterized as described in Example 3. Results of the kinetic measurement are shown in FIG. 6. For a given probe, time of hybridization deceases as the density of the immobilized oligonucleotide on the surface decreases (left to right across each row). For oligonucleotides HybC1 and HybC2, the time of hybridization (Tau) were plotted as a function of concentration (FIG. 7), revealing a linear dependence of Tau on concentration.

Figure 8A:
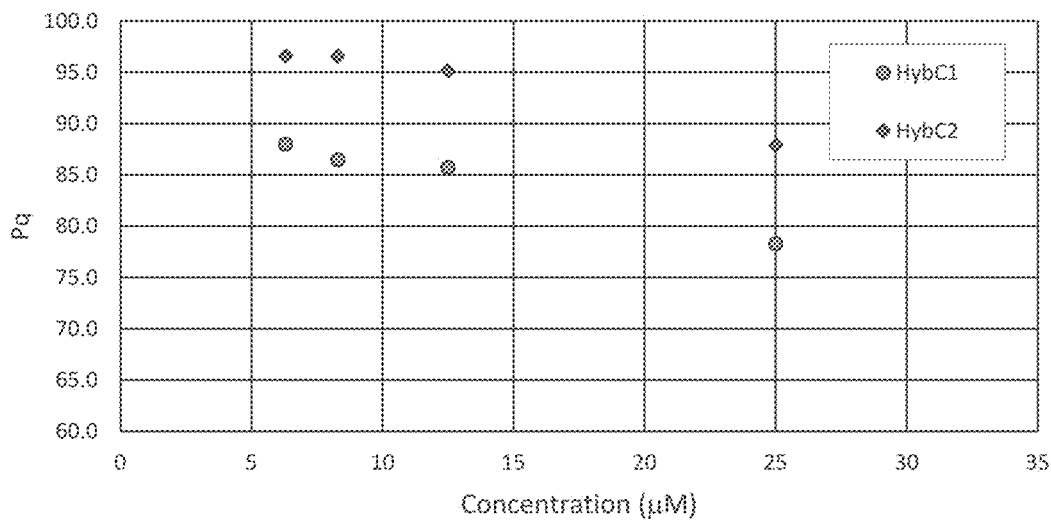
FIGS. 8A and 8B show percent quenching (Pq) of various surface-immobilize nucleic acid molecules as a function of printing concentration.
Figure 8B:
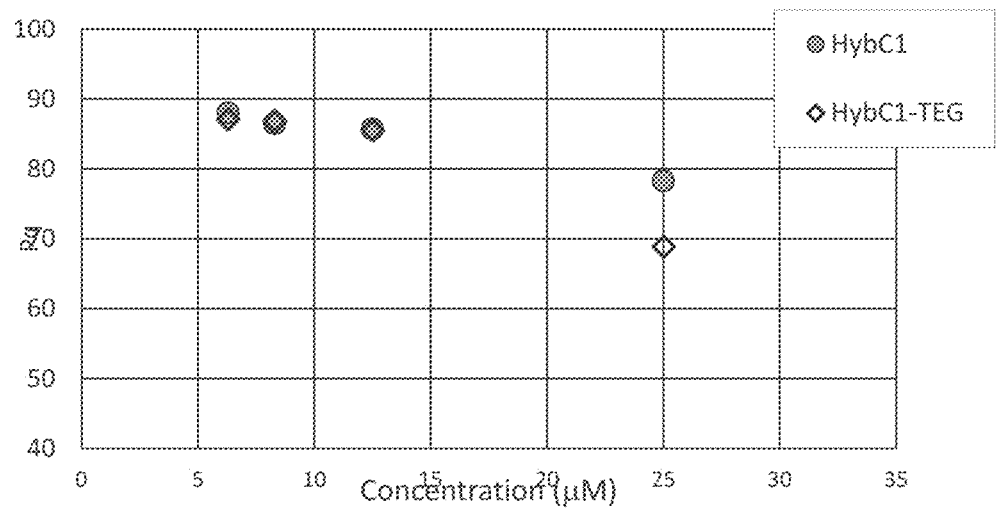
Figure 9A:
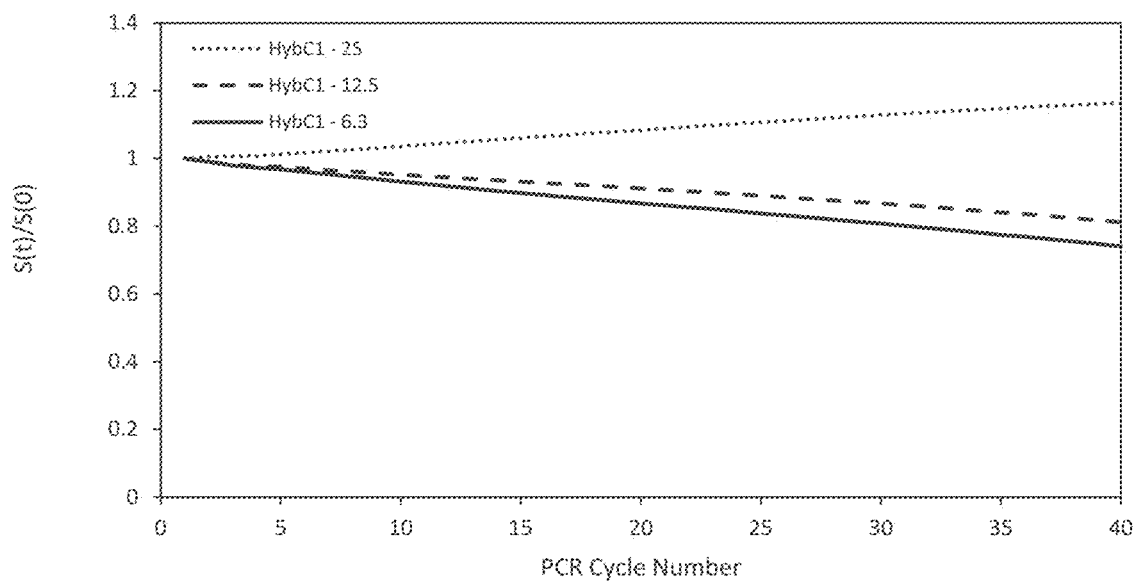
FIGS. 9A-9D show the change in fluorescence signal as a function of PCR cycle for various surface-immobilized nucleic acid molecules.
Figure 9B:
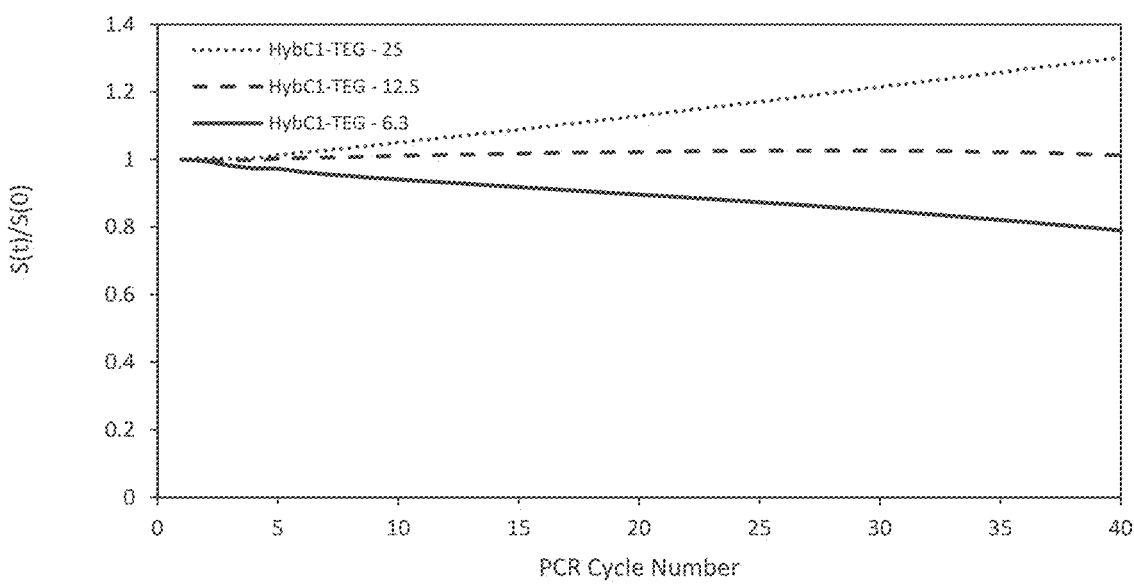
Figure 9C:
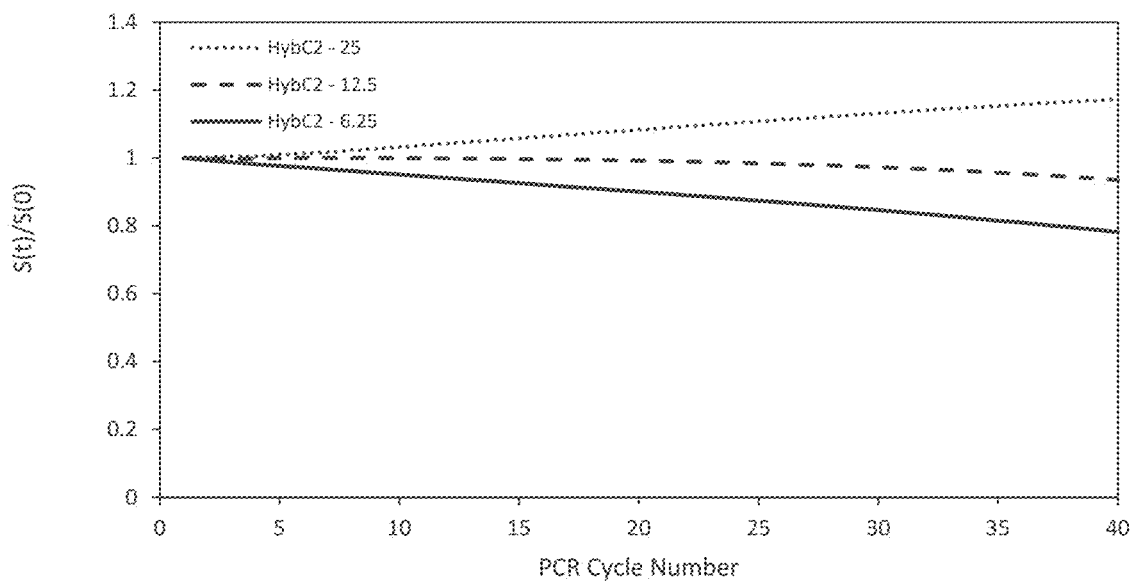
Figure 9D:
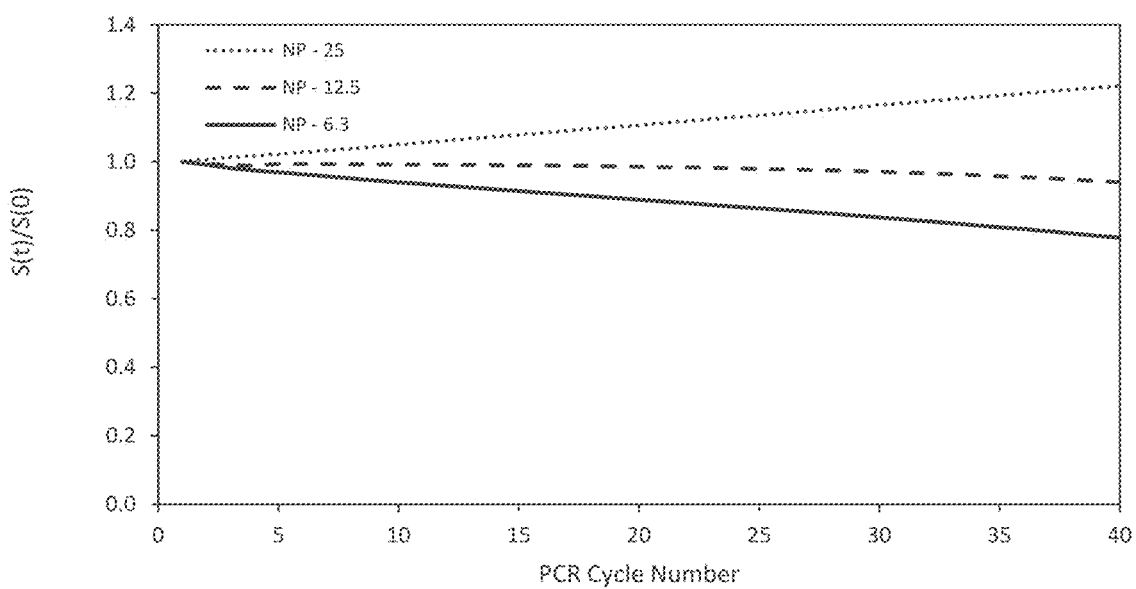

The percent quenching (Pq) of each probe was measured and plotted, as shown in FIGS. 8A and 8B. Pq was seen to decrease with decreasing concentration.

Additionally, the variation in fluorescence amplitude for each oligonucleotide as a function of PCR heating cycle is shown in FIGS. 9A-D. The particular profile of each curve depends on the concentration of oligonucleotide in the printing buffer. Depending on the particular application, one profile or another may be preferred.

Example 5: Introduction of Dibenzocyclooctyne (DBCO) Moiety into Oligonucleotides of Interest A DBCO moiety was introduced to a nucleic acid construct as described herein (e.g., a target oligonucleotide) according to Scheme A.

A solution of DBCO-sulfo-N-hydroxysuccinimidyl ester (0.510 µg, 1.00 nmol) in water (2 µL) was added to a solution of target oligonucleotide (1.60 nmol) in phosphate buffered saline (18 µL, pH=7.2). The reaction mixture was incubated at room temperature for 2 h. The reaction mixture was purified on a CENTRI-SEP Spin desalting column to purify the modified oligonucleotide.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for immobilizing a nucleic acid construct to a surface of a substrate, the method comprising:
   immobilizing a silane to the surface of the substrate, wherein the silane comprises a first chemical group; and
   contacting the silane with the nucleic acid construct comprising a second chemical group, wherein the contacting is performed for less than 10 minutes;
   wherein the substrate comprises an integrated optical sensor circuit comprising a complementary metal-oxide-semiconductor (CMOS) integrated circuit (IC), wherein (1) the first chemical group comprises a first alkyne and the second chemical group comprise a first azide; or (2) the first chemical group comprises a second azide and the second chemical group comprises a second alkyne, wherein the first and second alkyne is a dibenzocyclooctyne (DBCO), or a derivative thereof, wherein the first chemical group reacts with the second chemical group via a strain-promoted alkyne-azide cycloaddition (SPAAC), thereby immobilizing the nucleic acid construct on the surface of the substrate.

2. The method of claim 1, wherein the integrated optical sensor circuit is configured for optical transduction of a fluorescent signal.

3. The method of claim 1, wherein the immobilizing comprises depositing the silane onto the surface of the substrate.

4. The method of claim 3, wherein the depositing comprises a vapor deposition.

5. The method of claim 3, wherein the depositing comprises a liquid deposition.

6. The method of claim 1, wherein the silane further comprises an alkoxy moiety.

7. The method of claim 1, wherein (1) the first chemical group further comprises a first linker, or (2) the second chemical group further comprises a second linker.

8. The method of claim 1, wherein the contacting is carried out at neutral pH.

9. The method of claim 1, wherein the contacting is carried out at room temperature.

10. The method of claim 1, further comprising: washing the surface of the substrate.

11. The method of claim 1, further comprising: prior to the contacting, repeating the immobilizing with the silane or a different silane.

12. The method of claim 1, wherein the contacting further comprises contacting the silane with at least one additional nucleic acid construct.

13. The method of claim 1, wherein the silane comprises an alkyl chain comprising at least three carbon atoms, and wherein the first chemical group is substituted on the alkyl chain.

14. The method of claim 13, wherein the silane comprises a silane of Formula (I):

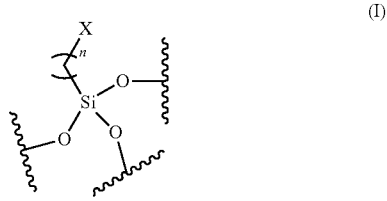

(I)

wherein n is an integer from 3-20 and X is the first chemical group.

* * * * *